(12) United States Patent  
Sugiura et al.

(10) Patent No.: US 8,384,044 B2
(45) Date of Patent: Feb. 26, 2013

(54) APPARATUS AND METHOD FOR READING FLUORESCENCE

(75) Inventors: Tadao Sugiura, Nara (JP); Masato Mori, Kyoto (JP); Eiji Inamoto, Kyoto (JP)

(73) Assignees: Japan Science and Technology Agency (JP); Nara Institute of Science and Technology (JP)

( * ) Notice: Subject to any disclaimer, the term of this patent is extended or adjusted under 35 U.S.C. 154(b) by 756 days.

(21) Appl. No.: 12/527,780

(22) PCT Filed: Aug. 27, 2007

(86) PCT No.: PCT/JP2007/000910
§ 371 (c)(1),
(2), (4) Date: Dec. 1, 2009

(87) PCT Pub. No.: WO2008/102417
PCT Pub. Date: Aug. 28, 2008

(65) Prior Publication Data
US 2010/0140503 A1 Jun. 10, 2010

(30) Foreign Application Priority Data
Feb. 19, 2007 (JP) .................................. 2007-038706

(51) Int. Cl.
*G01N 21/64* (2006.01)
(52) U.S. Cl. .............. 250/459.1; 250/458.1; 250/361 R; 250/483.1; 250/484.2; 359/388; 359/385; 435/287.2; 435/288.7
(58) Field of Classification Search ............... 250/459.1
See application file for complete search history.

(56) References Cited

U.S. PATENT DOCUMENTS
(Continued)

FOREIGN PATENT DOCUMENTS
JP 2001-194310 7/2001
JP 2005-30906 2/2005
(Continued)

OTHER PUBLICATIONS

English translation of the International Preliminary Report on Patentability for corresponding International Application No. PCT/JP2007/000910, mailed Sep. 3, 2009.

(Continued)

*Primary Examiner* — David Porta
*Assistant Examiner* — Djura Malevic
(74) *Attorney, Agent, or Firm* — Myers Wolin, LLC

(57) ABSTRACT

It is an objection of the present invention to provide a fluorescence reading apparatus in view of the influence of fluorescence derived from a fluorescence substance that is not involved with an interaction between a probe substance and a target substance.
The above-mentioned problem is solved by a fluorescence reading apparatus 12 comprising an incidence angle adjusting means 10 for adjusting an incidence angle when light from a light source 7 is incident on a substrate 2; and a controller 11 that controls an amount of the incidence angle adjusted by the incidence angle adjusting means 10 and also comprises a means for receiving information on the incidence angle and information on the fluorescence intensities or fluorescence images at a plurality of incidence angles and obtaining the penetration depths of the evanescent fields with respect to the plurality of incidence angles from the information on the incidence angles; and a means for obtaining information on the fluorescence intensities in the obtained plurality of penetration depths.

14 Claims, 16 Drawing Sheets

U.S. PATENT DOCUMENTS

| | | | |
|---|---|---|---|
| 5,585,242 A * | 12/1996 | Bouma et al. | 435/6.12 |
| 7,369,308 B2 * | 5/2008 | Tsuruta et al. | 359/388 |
| 2002/0123132 A1 | 9/2002 | Tanaami et al. | |
| 2003/0205681 A1 | 11/2003 | Modlin | |
| 2005/0174631 A1 | 8/2005 | Nishiwaki et al. | |
| 2006/0257290 A1 | 11/2006 | Shimizu | |
| 2006/0292686 A1 | 12/2006 | Fujikura | |
| 2008/0272313 A1 * | 11/2008 | Van Herpen et al. | 250/459.1 |
| 2010/0285490 A1 * | 11/2010 | Dees et al. | 435/7.1 |

FOREIGN PATENT DOCUMENTS

| | | |
|---|---|---|
| JP | 2005-106711 | 4/2005 |
| JP | 2005-121796 | 5/2005 |
| JP | 2006-38816 | 2/2006 |
| JP | 2006-105658 | 4/2006 |
| JP | 2006-189741 | 7/2006 |
| JP | 2006-317433 | 11/2006 |
| JP | 2007-3490 | 1/2007 |

OTHER PUBLICATIONS

International Search Report (with English translation) issued by the Japanese Patent Office as ISA for corresponding International Application No. PCT/JP2007/000910, mail date of Nov. 13, 2007.

* cited by examiner

Fig.7
Fig.7(a)
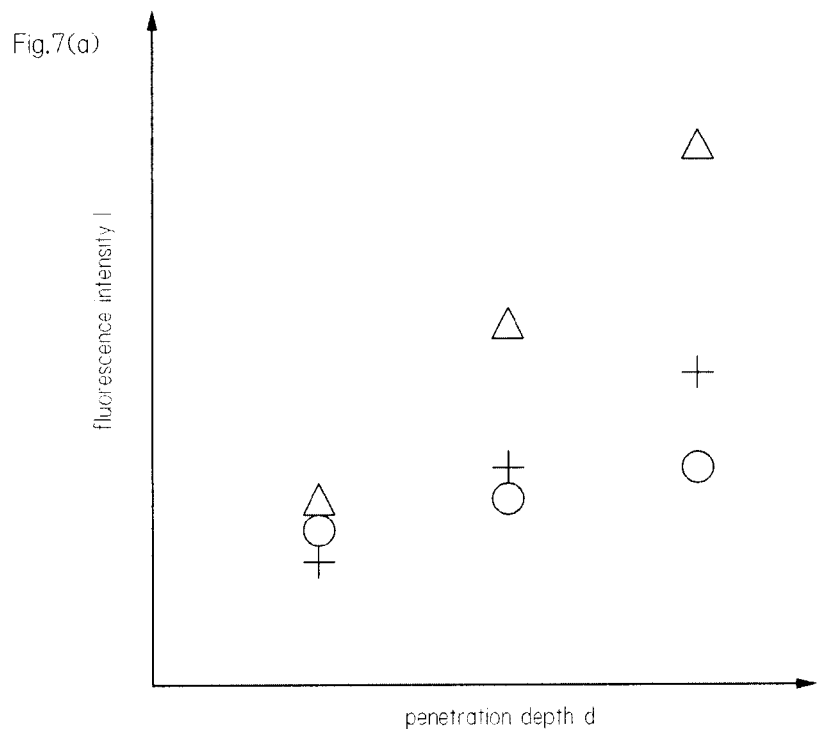
Fig.7(b)
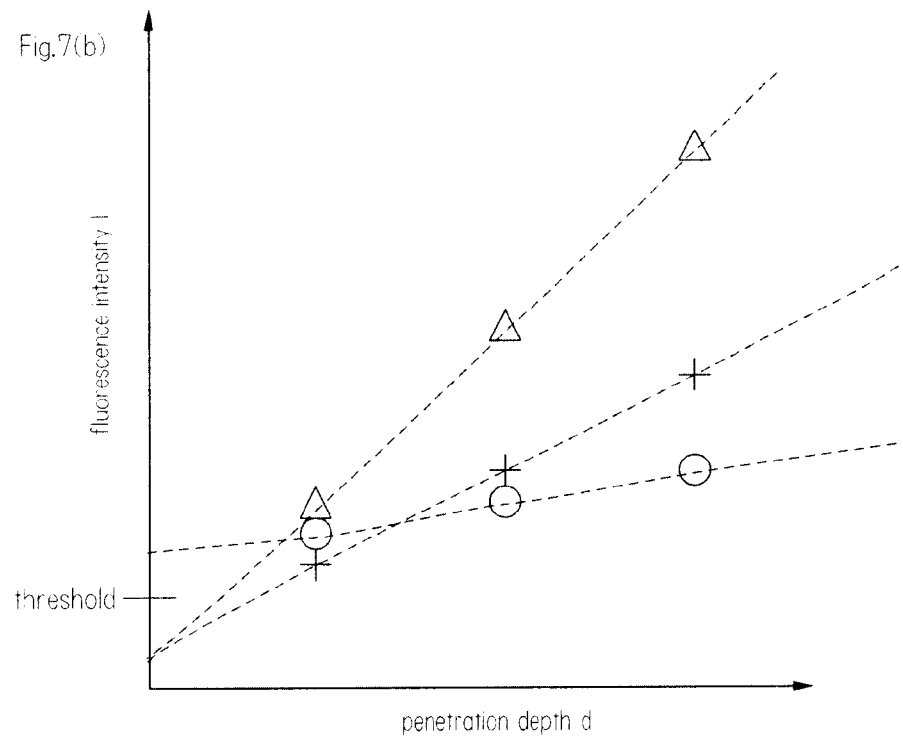

Fig.8
Fig.8(a)
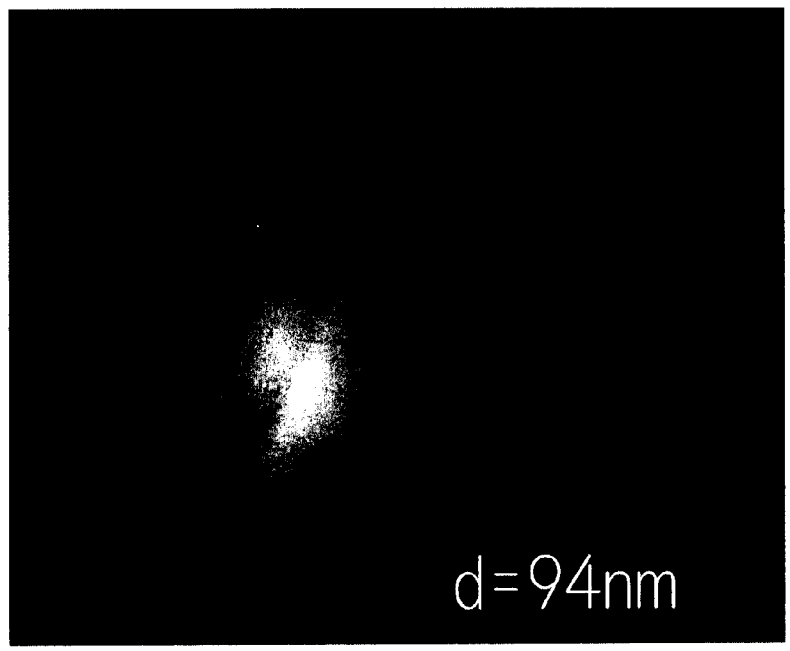
Fig.8(b)
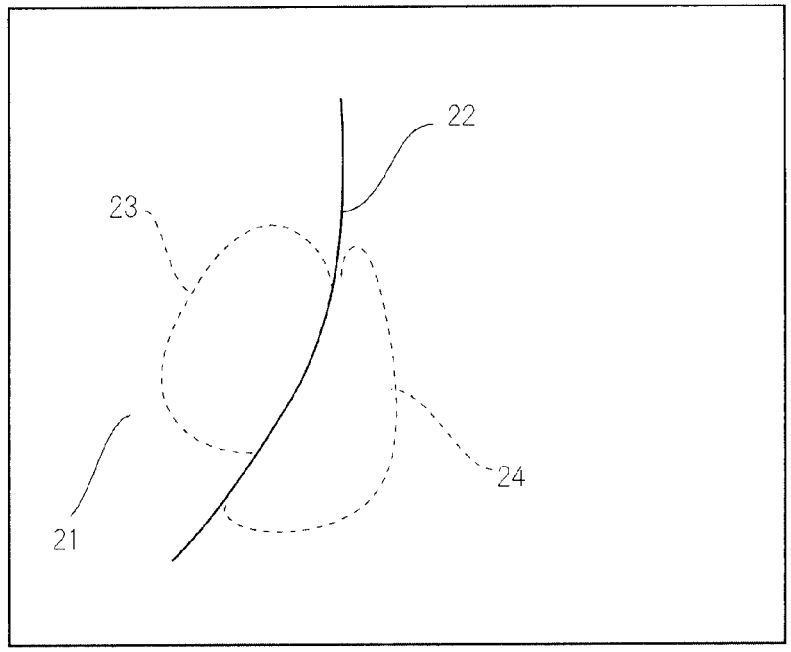

Fig.12
Fig.12(a)
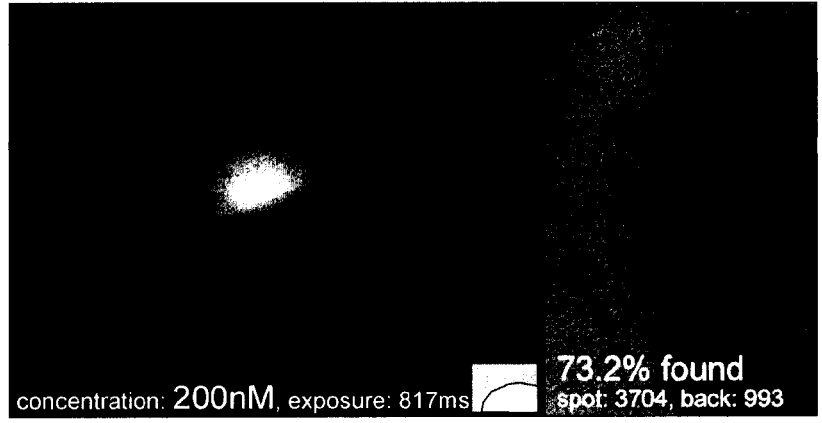
Fig.12(b)
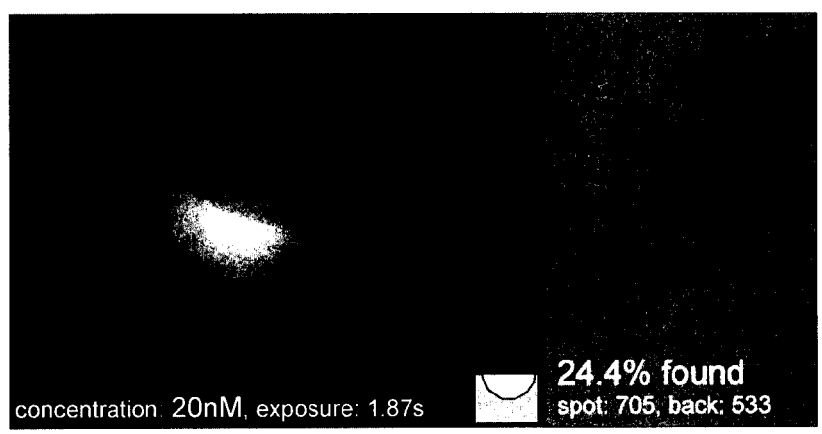
Fig.12(c)
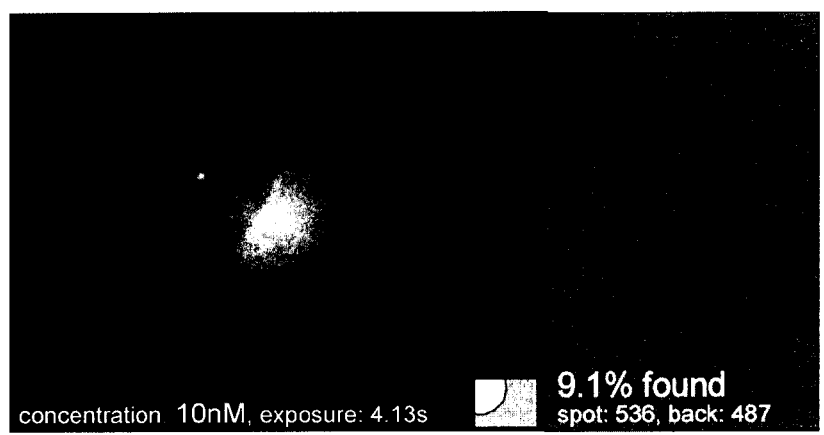

Fig.13
Fig.13(a)
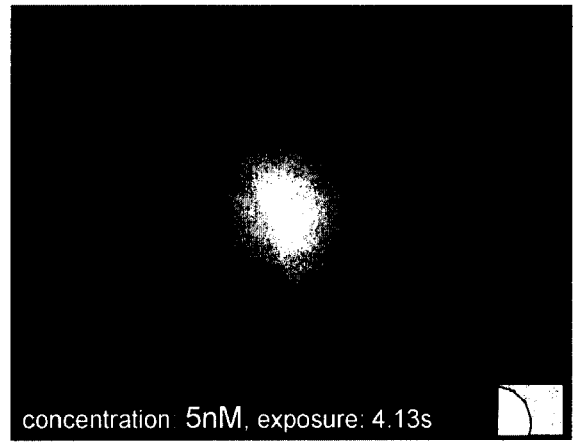
concentration 5nM, exposure: 4.13s
Fig.13(b)
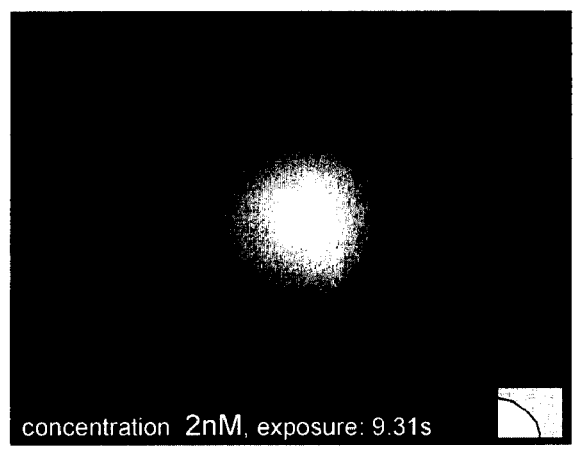
concentration 2nM, exposure: 9.31s
Fig.13(c)
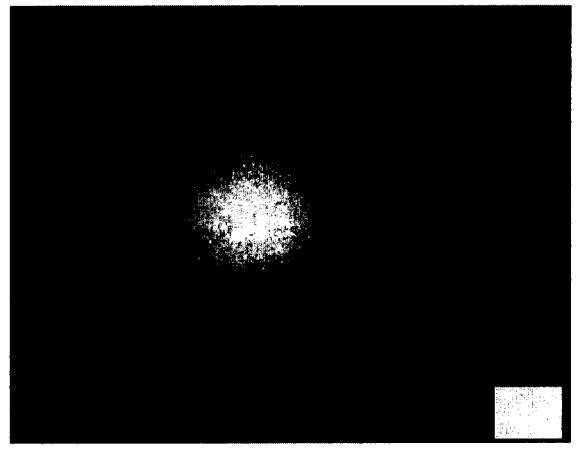

Fig.14
Fig.14(a)
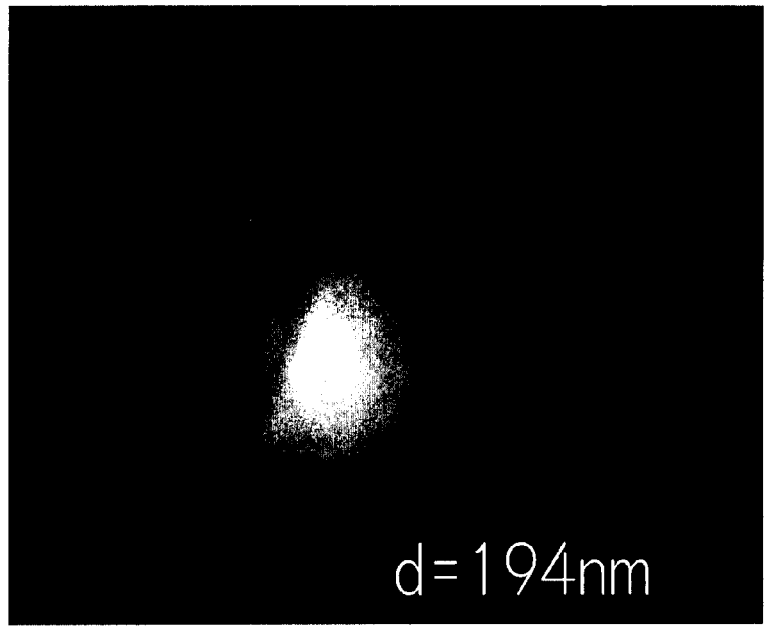
Fig.14(b)
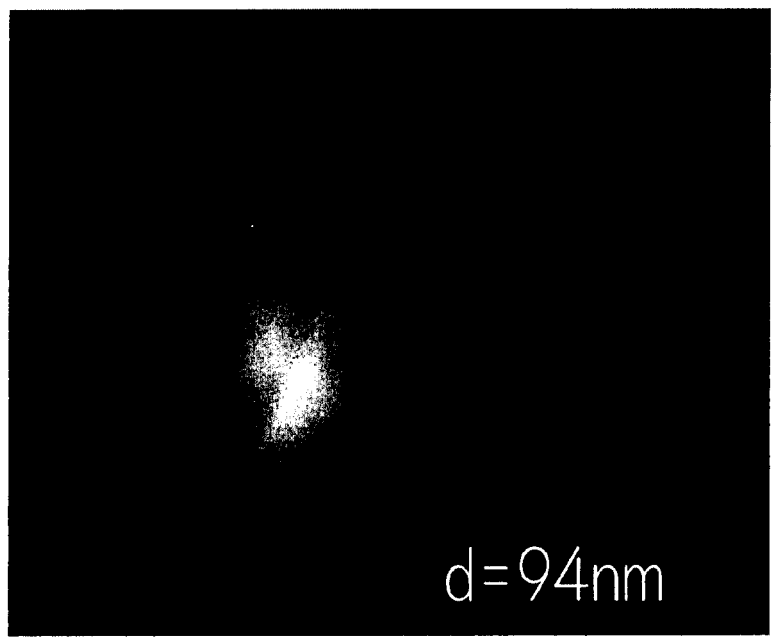

Fig.15
Fig.15(a)
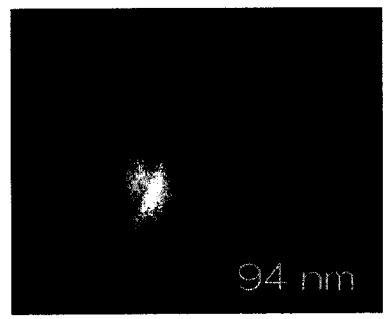
Fig.15(b)
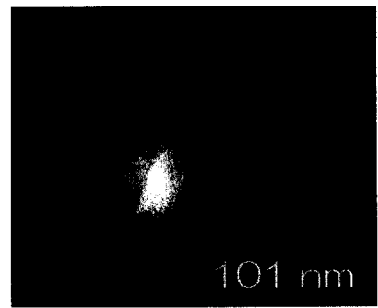
Fig.15(c)
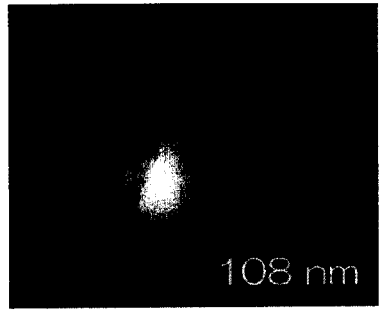
Fig.15(d)
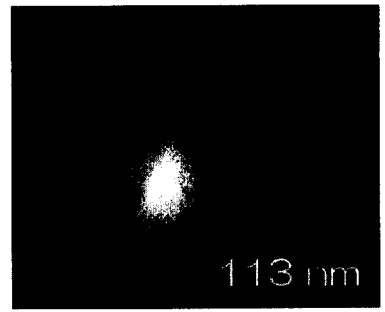
Fig.15(e)
Fig.15(f)
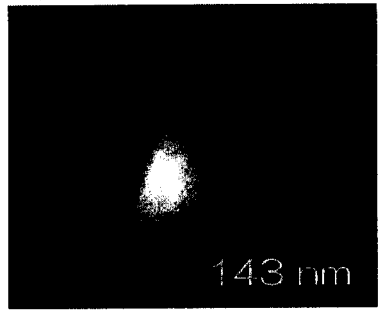
Fig.15(g)
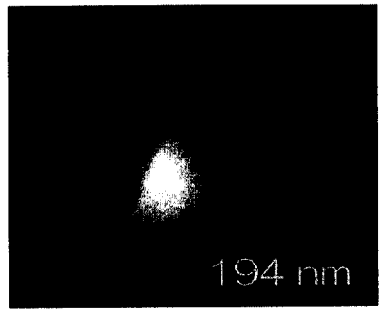

APPARATUS AND METHOD FOR READING FLUORESCENCE

CROSS REFERENCE TO RELATED APPLICATIONS

The present disclosure is a national phase filing under 35 U.S.C. §371 of International Patent Application No. PCT/JP2007/000910 filed on Aug. 27, 2007, which claims priority to Japanese Patent Application No. 2007-038706 filed on Feb. 19, 2007, the disclosures of which are expressly incorporated herein by reference in their entireties.

BACKGROUND OF THE INVENTION

1. Field of the Invention

The present invention relates to a fluorescence reading apparatus in view of the influence of fluorescence derived from a fluorescence substance that is not involved with an interaction between a probe substance and a target substance. More particularly, the invention relates to a microarray reading apparatus and a reading method, in which a penetration depth of an evanescent field is changed to obtain fluorescence intensities in a plurality of penetration depths, allowing an accurate determination whether the probe substance and the target substance have interacted with each other.

2. Description of the Related Art

In a DNA microarray, DNAs such as gene segments are arranged in and fixed to a substrate. For example, a plurality of gene segments are respectively fixed to spots to prepare a probe, and mRNA extracted from a human cell is converted into cDNA by a reverse transcriptase to obtain a target substance. In a DNA micro array reading apparatus, hybridization of the target substance and the probe fixed to the substrate is observed to analyze various genetic information. For example, a fluorescent substance is used in order to detect the interaction between the target substance and the probe substance. The fluorescent substance may be added to the target substance, or the fluorescent substance may generate fluorescence by the influence of the interaction between the target substance and the probe substance. As a fluorescence reading apparatus such as the microarray reading apparatus that observes the fluorescence derived from the fluorescent substance, there is an apparatus that generates the evanescent field in a region where the probe substance is fixed to excite the fluorescent substance, for example. In such case, it takes a long time to hybridize the target substance and the probe substance. Therefore, there is a demand for a real-time microarray reading apparatus that can detect a state of the interaction between the target substance and the probe substance.

To this end, for example, Japanese Patent Application Laid-Open No. 2006-38816 (Patent Document 1 below) discloses a microarray reading apparatus that detects the specific interaction between the probe substance and the target substance when a sample containing at least the fluorescent substance and the target substance is brought into contact with the substrate to which the probe substance is fixed. The microarray reading apparatus includes a light irradiation means for irradiating light; a light incident means for causing the light irradiated by the irradiation means to be incident on the substrate such that the evanescent field is generated in a surface of the substrate to which the probe substance is fixed; and a light detecting means for detecting the fluorescence generated from the fluorescent substance contained in the sample excited by the evanescent field. In the microarray reading apparatus, the light detecting means includes an optical lens that acts as an objective lens, and the optical lens acts as the light incident means.

The microarray reading apparatus disclosed in Japanese Patent Application Laid-Open No. 2006-38816 (Patent Document 1 below) is excellent in rapidly and accurately observing the hybridization of the target substance and the probe substance. However, disadvantageously the microarray reading apparatus observes not only the emission derived from the hybridization of the target substance and the probe substance but also a noise such as the fluorescence derived from the fluorescent substance flowing in a flow-through cell. That is, in the conventional real-time microarray reading apparatus, the evanescent field having intensity enough to excite the luminous material is generated in a region up to about 100 nm from a substrate surface. In the region within 100 nm from the substrate surface, there are many luminous materials that emit light irrespective of the interaction between the target substance and the probe substance because the sample containing the fluorescent substance is continuously brought into contact with the probe substance. Therefore, in the conventional microarray reading apparatus, because strong fluorescence is often observed even when the target substance and the probe substance do not hybridize with each other, a determination whether the target substance and the probe substance have interacted with each other cannot correctly be made.

Further, in the conventional micro array reading apparatus, because the emission caused only by the interaction between the target substance and the probe substance cannot be observed, an amount of the target substance interacting with the probe substance cannot quantitatively be evaluated.

Furthermore, in the conventional microarray reading apparatus, a distribution of the fluorescent substance generating the fluorescence, which indicates at which positions from the substrate the target substance and the probe substance have interacted with each other, is not recognized.

Japanese Patent Application Laid-Open No. 2006-189741 (Patent Document 2 below) discloses an invention in which an incidence angle adjusting means is controlled such that a leach-through depth of evanescent light is set to a desired amount (see, for example, claim 12). However, in the invention disclosed in this document, an incidence angle is controlled in order to keep the leach-through depth of evanescent light constant even if the laser beam sources are changed. That is, because the technique is essentially directed to keep the penetration depth of the evanescent field as constant as possible, the technique does not inspire fluorescence measurement in various penetration depths of the evanescent field.

Japanese Patent Application Laid-Open No. 2001-194310 (Patent Document 3 below) relates to a surface plasmon spectral apparatus in which a plurality of samples are measured at a time although only one objective lens is used.

U.S. Patent Application Publication No. 2003/0205681 (Patent Document 4 below) discloses a fluorescence analyzer in which a microarray is used. In the fluorescence analyzer, two penetration depths of evanescent fields are obtained using two light beams (paragraph [0069], claim 41). However, this document fails to disclose that the fluorescence is observed in a number of penetration depths of evanescent fields to effectively observe the presence or absence of the hybridization.

Patent Document 1: Japanese Patent Application Laid-Open No. 2006-38816
Patent Document 2: Japanese Patent Application Laid-Open No. 2006-189741

Patent Document 3: Japanese Patent Application Laid-Open No. 2001-194310

Patent Document 4: U.S. Patent Application Publication No. 2003/0205681

SUMMARY OF THE INVENTION

An object of the invention is to provide a fluorescence reading apparatus such as a microarray reading apparatus in view of the influence of the fluorescence derived from the fluorescent substance that is not involved with the interaction between the probe substance and the target substance.

An object of the invention is to provide a fluorescence reading apparatus such as a microarray reading apparatus that can compare the amount of target substances that have interacted with the probe substances.

An object of the invention is to provide a fluorescence reading apparatus that can also observe the distribution of the fluorescent substance generating the fluorescence.

An object of the invention is to provide a fluorescence reading apparatus that can also observe a temporal change in fluorescence intensity of the target substance that has interacted with the probe substance.

An object of the invention is to provide a fluorescence reading apparatus that solves a problem that the downstream region is lower than the upstream region in the concentration of the target substance because the target substance contained in the sample is sequentially bonded to the probe substance fixed to the substrate when the flow-through cell is used, and that can thus suppress unevenness of measuring conditions due to the difference in the concentration of the target substance between upstream and downstream regions in the flow-through cell.

Basically the invention is based on a knowledge that the penetration depth of the evanescent field is changed to obtain the fluorescence intensities in a plurality of penetration depths, and relationships between the fluorescence intensities and the penetration depths are plotted on a graph, allowing the accurate determination whether the probe substance and the target substance have interacted with each other.

A first aspect of the invention relates to a fluorescence reading apparatus 12 that detects a specific interaction between a probe substance and a target substance, the fluorescence reading apparatus including a substrate 2 to which the probe substance 1 is fixed; a sample chamber 6 that accommodates the probe substance 1 and also accommodates a sample 5 such that the sample is brought into contact with the probe substance 1, the sample containing a fluorescent substance 3 and the target substance 4; a light source 7; an optical system 8 that guides the light from the light source 7 to the substrate 2 to generate an evanescent field; and a fluorescence detecting unit 9 that detects a fluorescence intensity or a fluorescence image generated by the fluorescent substance 3 excited by the evanescent field, wherein the optical system 8 includes an incidence angle adjusting means 10 for adjusting an incidence angle when the light from the light source 7 is incident on the substrate 2; and a controller that controls an amount of the incidence angle adjusted by the incidence angle adjusting means 10.

Because the fluorescence reading apparatus in accordance with the invention includes the incidence angle adjusting means 10, the incidence angle is adjusted when the light is incident on the substrate. Therefore, the penetration depth of the evanescent field can be controlled. Further, because the fluorescence reading apparatus in accordance with the invention includes the controller, the penetration depth can be controlled, and the controlled penetration depth can be stored.

In the fluorescence reading apparatus 12 in accordance with the first aspect of the invention, the controller includes a means for receiving information on the incidence angle adjusted by the incidence angle adjusting means 10 and information on the fluorescence intensities or fluorescence images at a plurality of incidence angles detected by the fluorescence detecting unit 9 and obtaining the penetration depths of the evanescent fields with respect to the plurality of incidence angles from the information on the incidence angles; and a means for obtaining information on the fluorescence intensities in the obtained plurality of penetration depths.

In the fluorescence reading apparatus, by adjusting the incidence angle, the information on the fluorescence intensities in the plurality of penetration depths can be obtained while the penetration depths of the evanescent fields are controlled.

As will be described later, if the relationships between the penetration depths of the evanescent fields and the fluorescence intensities with respect to a plurality of penetration depths are obtained, a determination whether the observed fluorescence includes only noise fluorescence ("fluorescence derived from the fluorescent substance that is not involved with the interaction between the probe substance and the target substance 4") can be made. The amount of fluorescence derived from the noise fluorescence can be estimated in the observed fluorescence intensity, so that true fluorescence (fluorescence derived from the fluorescent substance involved with the interaction between the probe substance and the target substance) can quantitatively be grasped. The fluorescence intensity of only the fluorescence inside the spot can also be detected while the fluorescence outside the spot is removed. That is, the invention can provide a fluorescence reading apparatus in which the influence of the noise fluorescence can be considered.

In the above-described fluorescence reading apparatus 12 in accordance with the first aspect of the invention, preferably the optical system 8 includes an optical element 13 on which the light is incident from the light source 7; and an objective lens 14 on which the light transmitted through the optical element is incident, and the incidence angle adjusting means 10 includes an optical element moving means for moving the optical element 13 such that a position relative to the objective lens 14 is changed.

Because the fluorescence reading apparatus includes the optical element moving means, the position of the light incident on the objective lens 14 can be adjusted, by moving the optical element 13 away from the objective lens 14 in a constant direction or by bringing the optical element close to the objective lens 14 in a constant direction, for example. Therefore, the incidence angle of the outgoing light from the objective lens with respect to the substrate surface can be changed, so that the penetration depth of the evanescent field can also be controlled. The controller 11 controls the moving amount of the optical element (such as a lens and a mirror). The controller 11 can obtain information on the incidence angle and information on the penetration depth of the evanescent field using the information on the position of the optical element.

Any of the above-described fluorescence reading apparatus in accordance with the first aspect of the invention preferably includes a substrate moving means 15 for moving a position of the substrate 2.

When a microarray substrate is used as the substrate, a plurality of spots are provided in the microarray, and various probe substances are fixed to each spot. Because the fluorescence reading apparatus includes the substrate moving means 15, the substrate 2 can be moved such that the evanescent field is generated in each spot. Therefore, the fluorescence intensities of various probe substances can be observed. When the plurality of spots are provided in the substrate 2, the controller 11 controls and grasps the information on the position of each spot and the information on the spot of which the fluorescence is currently observed.

In any of the above-described fluorescence reading apparatus 12 in accordance with the first aspect of the invention, preferably the controller includes a means for obtaining a graph, using relationships between the penetration depths of the evanescent fields and the fluorescence intensities with respect to a plurality of penetration depths, in which one (for example, vertical axis) of axes represents the fluorescence intensity while the other axis (for example, horizontal axis) represents the penetration depth of the evanescent field in the graph.

The fluorescence reading apparatus supplies the information on the obtained graph to a display device such as a monitor, and the graph is displayed on the display device. According to the fluorescence reading apparatus, since the graph in which one of the axes represents the fluorescence intensity while the other axis represents the penetration depth of the evanescent field is displayed using the relationships between the penetration depths of the evanescent fields and the fluorescence intensities with respect to a plurality of penetration depths, the determination whether the observed fluorescence includes only noise fluorescence ("fluorescence derived from the fluorescent substance that is not involved with the interaction between the probe substance and the target substance") can easily visually be made. That is, a user sees the graph to estimate the state in which each observation point is plotted. When only the noise fluorescence (fluorescence derived from the fluorescent substance only that is not involved with the interaction between the probe substance and the target substance) is observed, an intercept when the penetration depth is zero becomes equal to or lower than a threshold. Therefore, according to the fluorescence reading apparatus, the influence of the noise fluorescence can be considered.

In any of the above-described fluorescence reading apparatus 12 in accordance with the first aspect of the invention, preferably the controller includes a means for obtaining a graph, using relationships between the penetration depths of the evanescent fields and the fluorescence intensities with respect to a plurality of penetration depths, in which one of axes represents the fluorescence intensity while the other axis represents the penetration depth of the evanescent field in the graph; a means for obtaining a hypothetical fluorescence intensity using each point on the graph when the penetration depth of the evanescent field is zero; a means for comparing a set threshold and the hypothetical fluorescence intensity when the penetration depth of the evanescent field is zero; and a means for determining whether the probe substance 1 and the target substance 4 have interacted with each other using the comparison result.

According to the fluorescence reading apparatus 12, a determination whether the probe substance and the target substance have interacted with each other can automatically be made. A criterion for the determination can appropriately be changed by correcting the set threshold.

In any of the above-described fluorescence reading apparatus 12 in accordance with the first aspect of the invention, preferably the controller includes a means for observing elapsed time.

According to the fluorescence reading apparatus 12, a fluorescence intensity of a certain spot can be observed for a plurality of times, so that the temporal change in fluorescence intensity of the spot can be observed. Therefore, the final interaction amount can be predicted while how the interaction such as the hybridization proceeds can be observed.

In any of the above-described fluorescence reading apparatus 12 in accordance with the first aspect of the invention, preferably the substrate 2 includes a spot 21 to which the probe substance 1 is fixed, the fluorescence detecting unit 9 obtains the fluorescence image generated by the fluorescent substance 3, and the controller 11 includes a means for scanning the fluorescence image to compute a boundary 21 at which the fluorescence intensity is changed; a means for grasping a region 23 inside the spot and a region 24 outside the spot in the fluorescence image from the shape of the boundary; and a means for obtaining the fluorescence intensity inside the spot.

Generally, when a fluorescence image of a certain spot is obtained, sometimes the fluorescence image includes both the inside of the spot and the outside of the spot. In such case, sometimes the fluorescence from the outside of the spot is higher than the fluorescence from the inside of the spot in intensity. Because the probe substance is not fixed to the outside of the spot, the fluorescence from the outside of the spot is deemed to be a noise component. Accordingly, when the fluorescence intensity is directly analyzed from the fluorescence image, the interaction between the probe substance and the target substance cannot correctly be grasped. On the other hand, in the fluorescence reading apparatus 12, the boundary between the inside of the spot and the outside of the spot is grasped from the fluorescence image, and the fluorescence intensity inside the spot is obtained, so that the interaction can be grasped more accurately than in a conventional art.

In any of the above-described fluorescence reading apparatus 12 in accordance with the first aspect of the invention, preferably the concentration of the probe substance is increased toward the downstream region of the sample chamber in the substrate 2 to which the probe substance 1 is fixed. In the case where the flow-through cell is used, the target substance contained in the sample is sequentially bonded to the probe substance fixed to the substrate, which causes the problem that the downstream region is lower than the upstream region in the concentration of the target substance. On the other hand, the fluorescence reading apparatus in accordance with the invention can suppress the unevenness of the measuring condition due to the difference in the concentration of the target substance between the upstream and downstream regions in the flow-through cell.

In any of the above-described fluorescence reading apparatus 12 in accordance with the first aspect of the invention, preferably not only a connecting pipe is connected to the uppermost-stream region of the sample chamber, but also one or more connecting pipes are connected to the midstream region of the sample chamber, the connecting pipe connecting the sample chamber and a sample storage in which the target substance is stored. In the case where the flow-through cell is used, the target substance contained in the sample is sequentially bonded to the probe substance fixed to the substrate, which causes the problem that the downstream region is lower than the upstream region in the concentration of the target substance. On the other hand, the fluorescence reading apparatus in accordance with the invention can suppress the unevenness of the measuring condition due to the difference in the concentration of the target substance between the upstream and downstream regions in the flow-through cell.

Any of the above-described fluorescence reading apparatus in accordance with the first aspect of the invention preferably includes a plurality of objective lenses and an optical system that guides light to the plurality of objective lenses. That is, the evanescent fields are generated at a plurality of points using the plurality of objective lenses for one substrate, so that the hybridization states can simultaneously be observed for the plurality of probe substances.

Any of the above-described fluorescence reading apparatus in accordance with the first aspect of the invention preferably includes a sample storage in which the target substance is stored; and a connecting pipe that connects the sample storage and a plurality of sample chambers, wherein the connecting pipe has a branch portion, and the downstream portions of each connecting pipe branched by the branch portion of the connecting pipe are connected to the plurality of sample chambers respectively. Since the fluorescence reading apparatus includes the plurality of sample chambers and each of the sample chambers has the observation system in this manner, the hybridization states can simultaneously be observed for the plurality of probe substances.

A second aspect of the invention relates to a fluorescence reading method using a fluorescence reading apparatus that detects a specific interaction between a probe substance and a target substance, the fluorescence reading apparatus including a substrate 2 to which the probe substance 1 is fixed; a sample chamber 6 that accommodates the probe substance 1 and also accommodates a sample 5 such that the sample is brought into contact with the probe substance 1, the sample containing a fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field, wherein a step of changing a penetration depth of the evanescent field and a step of obtaining the fluorescence intensity after the penetration depth of the evanescent field is changed are repeatedly performed to obtain the fluorescence intensities in a plurality of penetration depths of the evanescent fields.

As will be described later, a determination whether the observed fluorescence includes only noise fluorescence can be made when relationships between the penetration depths of the evanescent fields and the fluorescence intensities with respect to a plurality of penetration depths are obtained. The amount of fluorescence derived from the noise fluorescence is estimated in the observed fluorescence intensity, so that true fluorescence can quantitatively be grasped. The fluorescence intensity of only the fluorescence inside the spot can be detected while the fluorescence outside the spot is considered. That is, the invention can provide a fluorescence reading method in which the influence of the noise fluorescence can be considered.

In the fluorescence reading method in accordance with the second aspect of the invention, preferably, in the step of changing the penetration depth of the evanescent field, the penetration depth of the evanescent field is changed by adjusting the incidence angle of the light incident on the substrate 2. As demonstrated in the embodiments described below, the penetration depth of the evanescent field can be changed by adjusting the incidence angle of the light incident on the substrate 2, so that the fluorescence intensity can easily be obtained in a plurality of penetration depths of the evanescent fields.

In any of the above-described fluorescence reading method in accordance with the second aspect of the invention, preferably a graph in which one of axes (for example, vertical axis) represents the fluorescence intensity while the other axis (for example, horizontal axis) represents the penetration depth of the evanescent field is obtained using relationships between the penetration depths of the evanescent fields and the fluorescence intensities with respect to the plurality of penetration depths. The graph in which one of the axes represents the fluorescence intensity while the other axis represents the penetration depth of the evanescent field can be displayed using the relationships between the penetration depths of the evanescent fields and the fluorescence intensities with respect to a plurality of penetration depths, so that the determination whether the observed fluorescence includes the noise fluorescence can easily visually be made. That is, the user sees the graph to estimate the state in which each observation point is plotted. When only the noise fluorescence is observed, the intercept when the penetration depth is zero becomes equal to or lower than a threshold. Accordingly, in the fluorescence reading method, the influence of the noise fluorescence can be considered.

In any of the above-described fluorescence reading method in accordance with the second aspect of the invention, preferably the substrate 2 includes a spot to which the probe substance 1 is fixed, relationships between the penetration depths of the evanescent fields and the fluorescence intensities with respect to a plurality of penetration depths are obtained for a certain spot 21, and then the relationships between the penetration depths of the evanescent fields and the fluorescence intensities with respect to the plurality of penetration depths are obtained for the spot 21 after a predetermined time has elapsed. In the fluorescence reading method, a fluorescence intensity of a certain spot can be observed for a plurality of times, so that the temporal change in fluorescence intensity of the spot can be observed. Therefore, the final interaction amount can be predicted while how the interaction such as the hybridization proceeds can be observed.

A third aspect of the invention relates to a fluorescence reading apparatus 12 that detects a specific interaction between a probe substance and a target substance, the fluorescence reading apparatus including a substrate 2 to which the probe substance 1 is fixed; a sample chamber 6 that accommodates the probe substance 1 and also accommodates a sample 5 such that the sample is brought into contact with the probe substance 1, the sample containing the fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field, wherein the concentration of the probe substance is increased toward the downstream region of the sample chamber in the substrate 2 to which the probe substance 1 is fixed.

A fourth aspect of the invention relates to a fluorescence reading apparatus 12 that detects a specific interaction between a probe substance and a target substance, the fluorescence reading apparatus including a substrate 2 to which the probe substance 1 is fixed; a sample chamber 6 that accommodates the probe substance 1 and also accommodates a sample 5 such that the sample is brought into contact with the probe substance 1, the sample containing a fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field, the fluorescence reading apparatus further including a sample storage in which the target substance is stored; and a connecting pipe that connects the sample storage and the sample chamber, wherein not only the connecting pipe is connected to an uppermost-stream region of the sample chamber, but also one or more connecting pipes are connected to a midstream region of the sample chamber.

A fifth aspect of the invention relates to a fluorescence reading apparatus 12 that detects a specific interaction between a probe substance and a target substance, the fluorescence reading apparatus including a substrate 2 to which the probe substance 1 is fixed; a sample chamber 6 that accommodates the probe substance 1 and also accommodates a sample 5 such that the sample is brought into contact with the probe substance 1, the sample containing a fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field, the fluorescence reading apparatus including a sample storage in which the target substance is stored; and a connecting pipe that connects the sample storage and a plurality of sample chambers, wherein the connecting pipe has a branch portion, and downstream portions of each connecting pipe branched by the branch portion of the connecting pipe are connected to the plurality of sample chambers.

In the invention, the penetration depth of the evanescent field is changed to obtain the fluorescence intensities in the plurality of penetration depths. The relationships between the fluorescence intensities and the penetration depths are plotted on the graph. When only the noise fluorescence is observed, the intercept when the penetration depth is zero becomes equal to or lower than the threshold. Accordingly, the invention can provide a fluorescence reading apparatus in which the influence of the noise fluorescence can be considered.

According to the invention, as described above, the influence of the noise fluorescence can be grasped, so that the true fluorescence can be grasped by subtracting the fluorescence intensity derived from the noise fluorescence from the actually-observed fluorescence. Accordingly, the invention can provide a fluorescence reading apparatus that can compare the amounts of target substances interacting with the probe substances.

In the invention, the true fluorescence can be grasped, and the fluorescence intensities can be obtained in the plurality of penetration depths by changing the penetration depth of the evanescent field. Accordingly, the invention can provide a fluorescence reading apparatus that can observe the distribution of the fluorescent substance generating the fluorescence.

According to the invention, the fluorescence reading apparatus includes a timing means. Accordingly, the invention can provide a fluorescence reading apparatus that can observe the temporal change of the target substance interacting with the probe substance.

The invention can provide a fluorescence reading apparatus that can suppress the unevenness of the measuring condition due to the difference in the concentration of the target substance between the upstream and downstream regions in the flow-through cell.

BRIEF DESCRIPTION OF THE DRAWINGS

FIG. 7 is an example of a graph showing observation data at a certain observation point, in which a vertical axis represents a fluorescence intensity while a horizontal axis represents a penetration depth of an evanescent field. FIG. 7A shows raw observation data, and FIG. 7B is a graph in which the observation data is plotted.

FIG. 8 illustrate an example of an observed fluorescence image. FIG. 8A is a photograph in place of a drawing illustrating an example of the observed fluorescence image, and FIG. 8B illustrates a boundary obtained using the image of FIG. 8A, the fluorescence intensity being changed at the boundary.

FIG. 12 shows photographs in place of a drawing illustrating an observed fluorescence image and microarray when the concentration of a fluorescent substance and an irradiation time are changed, where the concentration is 200 nM and the irradiation time is 817 ms in FIG. 12A, the concentration is 20 nM and the irradiation time is 1.87 s in FIG. 12B, and the concentration is 10 nM and the irradiation time is 4.13 s in FIG. 12C.

FIG. 13 shows photographs in place of a drawing illustrating an observed fluorescence image and a microarray when the concentration of a fluorescent substance and an irradiation time are changed, where the concentration is 5 nM and the irradiation time is 4.13 s in FIG. 13A, the concentration is 2 nM and the irradiation time is 9.31 s in FIG. 13B, and the concentration is 1 nM and the irradiation time is 9.31 s in FIG. 13C.

FIG. 14 shows photographs in place of a drawing illustrating an example of the observed fluorescence image, where a penetration depth is 194 nm in FIG. 14A, and the penetration depth is 94 nm in FIG. 14B.

FIG. 15 shows photographs in place of a drawing illustrating an example of the observed fluorescence image when the penetration depth is changed, where the penetration depth is 94 nm in FIG. 15A, the penetration depth is 101 nm in FIG. 15B, the penetration depth is 108 nm in FIG. 15C, the penetration depth is 113 nm in FIG. 15D, the penetration depth is 123 nm in FIG. 15E, the penetration depth is 143 nm in FIG. 15F, and the penetration depth is 194 nm in FIG. 15G.

EXPLANATION OF THE NUMERALS

| | |
|---|---|
| 1 | Probe substance |
| 2 | Substrate |
| 3 | Fluorescent substance |
| 4 | Target substance |
| 5 | Sample |

-continued

| EXPLANATION OF THE NUMERALS | |
|---|---|
| 6 | Sample chamber |
| 7 | Light source |
| 8 | Optical system |
| 9 | Fluorescence detecting unit |
| 10 | Incidence angle adjusting means |
| 11 | Controller |
| 12 | Fluorescence reading apparatus |

DETAILED DESCRIPTION OF THE INVENTION

Figure 1:
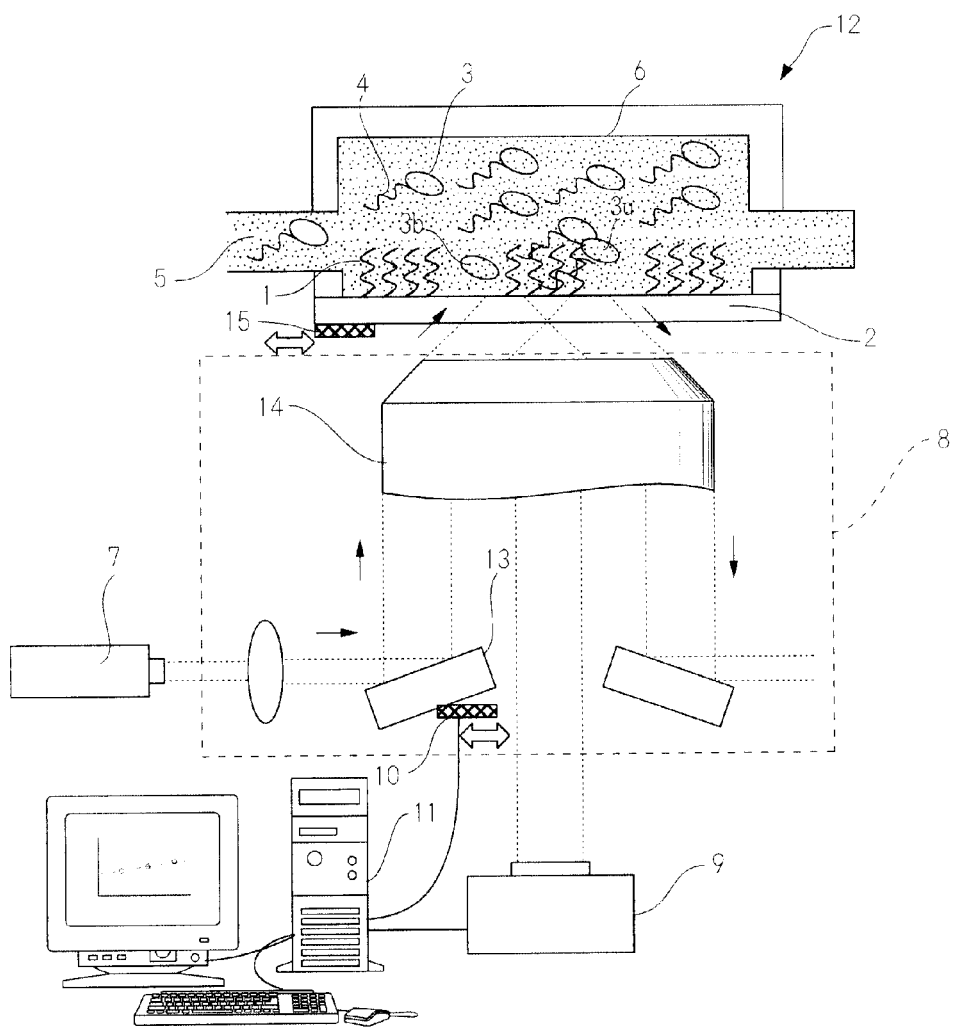
FIG. 1 schematically illustrates a configuration of a fluorescence reading apparatus according to the invention.

1 Basic Configuration of Fluorescence Reading Apparatus According to the Invention Hereinafter, the invention will specifically be described with reference to the drawings. FIG. 1 schematically illustrates a configuration of a fluorescence reading apparatus according to the invention. Referring to FIG. 1, the fluorescence reading apparatus according to the first aspect of the invention that detects a specific interaction between a probe substance 1 and a target substance 4 basically includes a substrate 2 to which the probe substance 1 is fixed; a sample chamber 6 that accommodates the probe substance 1 and also accommodates a sample 5 such that the sample 5 is brought into contact with the probe substance 1, the sample containing a fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field. In the fluorescence reading apparatus, the optical system 8 includes an incidence angle adjusting means 10 that adjusts an incidence angle when the light from the light source 7 is incident on the substrate 2; and a controller 11 that controls an amount of incidence angle adjusted by the incidence angle adjusting means 10.

Because the incidence angle adjusting means 10 is provided, the incidence angle can be adjusted when the light is incident on the substrate. Therefore, the penetration depth of the evanescent field can be controlled. Further, because the controller 11 is provided, the relationships between the penetration depths of the evanescent fields and the fluorescence intensities with respect to a plurality of penetration depths can be obtained.

As will be described later, if the relationships between the penetration depths of the evanescent fields and the fluorescence intensities with respect to a plurality of penetration depths are obtained, a determination whether the observed fluorescence is the noise fluorescence (fluorescence derived from the fluorescent substance that is not involved with the interaction between the probe substance and the target substance) can be made. The amount of fluorescence derived from the noise fluorescence can be estimated in the observed fluorescence intensity, so that the true fluorescence can quantitatively be grasped. That is, the invention can provide a fluorescence reading apparatus in which the influence of the noise fluorescence can be considered.

1.1 Fluorescence Reading Apparatus

The fluorescence reading apparatus is an apparatus that detects a specific interaction between the probe substance and the target substance. The microarray reading apparatus that are examples of the fluorescence reading apparatus are publicly known, and the techniques regarding the publicly known microarray can be employed in the invention with appropriate modifications thereto. Examples of the techniques regarding the microarray are disclosed, for example, in Tadao Sugiura, "Next-Generation DNA Microarray Measuring Technology", BME, Vol. 18, No. 3, pp. 29-36 (2004), Kaori Haruna, Tadao Sugiura, Tetsuhiro Sato, Yoshito Tabata, and Kotaro Minato, "Real-Time Detection of Hybridization Process in DNA Microarray", Seitaiikougaku (the Japanese Society for Medical and Biological Engineering) 41 (Suppl.), 148, 2003, and Carolin Peter et al., "Optical DNA-sensor chip for real-time detection of hybridization events" Fresenius J. Anal. Chem. (2001), Vol. 371, pp. 120-127.

1.2 Substrate

The substrate is one to which the probe substance is fixed. Specific examples of the substrate include a microarray substrate. Because the microarray technique is publicly known, a publicly known substrate used in the microarray, for example, can appropriately be used in the invention. Because the microarray substrate is commercially available, the commercial microarray substrate may be used. The substrate is one to which the probe substance is fixed. The probe substance is a publicly known substance, and may interact specifically with a target substance contained in a sample when the probe substance comes into contact with the sample containing the target substance. The target substance can be detected by utilizing the presence or absence of the interaction.

In the case where a flow-through cell is used, the target substance contained in the sample is sequentially bonded to the probe substance fixed to the substrate, which causes a problem that the concentration of the target substance is lower in the downstream region than in the upstream region. Because the concentration of the target substance is different between the downstream region and the upstream region, the interaction between the target substance and the probe cannot be measured under homogeneous conditions. Therefore, in a preferred embodiment of the invention, the concentration of the probe substance is increased toward the downstream region of the sample chamber. Specifically, a density of the fixed probe substance may be increased toward the downstream region, or a size of a spot in which the probe is provided may be increased toward the downstream region. Alternatively, the substrate may be divided into two or more regions, and the probe concentration may be increased toward the downstream region in each region. Therefore, the unevenness of the measuring conditions due to the difference in the concentration of the target substance between the upstream and downstream regions in the flow-through cell can be suppressed.

Assuming that v is a flow velocity at which a sample solution is transported and τ is a time constant when the concentration of the target molecules are decreased by molecule adsorption, the probe density $g(x)$ in the spot located at a distance x from the upstream region is preferably adjusted to satisfy $g(x)=g_0 \exp(x/(v\tau))$, where $g_0$ is a probe density in the spot on the uppermost-stream side (x=0). In order to modulate the concentration of the probe, the concentration of the probe contained in a spotting solution used in spotting may be adjusted. The above equation is obtained as follows. The state in which the sum of the target molecules in the sample solution is decreased by the molecule adsorption is expressed by $p(t)=p_0 \exp(-t/\tau)$, where $p_0$ is an initial value of the number of molecules. Assuming that the sample is transported at the velocity v, because a time x/v elapses until the sample reaches the position at the distance x from the upstream region, the number of target molecules $P(x)$ at the position is $P(x)=p_0 \exp(-x/(v\tau))$. The number of target molecules adsorbed in the spot is expressed by a product of the number of molecules P(x) in the target solution and the density g(x) of the probe molecules in the spot. Therefore, in order to maintain the number of target molecules adsorbed in the spot at a constant value irrespective of the position, desirably the density of the probe molecules in the spot is adjusted according to the equation.

Figure 2:
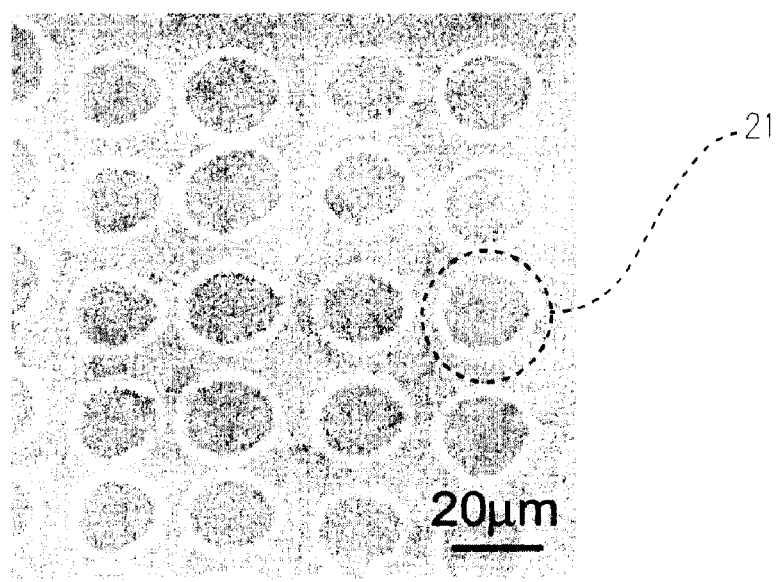
FIG. 2 is a photograph in place of a drawing illustrating an example of a surface of a substrate.

FIG. 2 is a photograph in place of a drawing illustrating an example of a surface of a substrate. As shown in FIG. 2, preferably the substrate is one in which a plurality of spots 21 are provided, that is, a microarray substrate. Preferably a plurality of kinds of probe substances are fixed to the substrate. The spot in the microarray substrate of FIG. 2 has a spot size of about 20 µm in diameter. However, the spot size may be any sized used in the publicly known substrate. Specifically, for example, the diameter may range from 10 µm to 1000 µm. Obviously the spot may have not only a circular shape but also ellipsoidal, square, rectangular, or rhombic shape.

In a preferred embodiment of the invention, the fluorescence is generated in the sample chamber, and the fluorescence is observed through the substrate. Therefore, preferably the substrate has optical transparency. Specific examples of the substrate material include glass, polycarbonate, or PMMA. Among others, the glass substrate is preferably used because the glass substrate has a small variation in refractive index by heat.

Because a publicly known substrate can appropriately be used, a substrate size may be appropriately adjusted, and is not limited to any particular size.

The probe substance fixed to the substrate includes publicly known substances such as a gene segment. Examples of the probe substance include nucleic acids such as DNA, RNA, polynucleotide, and oligonucleotide, peptide, polypeptide, protein, and antibody. Among others, single-stranded DNA is preferably used as the probe substance. When single-stranded DNA is used, for example, cDNA obtained by reverse transcription of obtained RNA can be used as the target substance to detect whether the hybridization occurs. For example, a size of DNA used as the probe substance may range from tens of bases to thousands of bases. A size of the oligonucleotide may range from 10 mer to 100 mer, and preferably from about 20 mer to 25 mer. The nucleotide is previously designed with a computer to specify a gene specific base sequence and obtained by synthesizing.

An amount of probe substance fixed to the substrate may appropriately be adjusted according to a publicly known method. A method of fixing the probe substance to the substrate is also publicly known. For example, the method of fixing the probe substance to the substrate includes a method of fixing previously-prepared oligonucleotide to a predetermined position on a slide glass using a spotter.

1.3 Sample

The sample used in the invention contains at least the fluorescent substance 3 and the target substance 4. A publicly known fluorescent substance and target substance, used in the microarray technique, can appropriately be employed as the fluorescent substance 3 and the target substance 4. Similarly, publicly known concentrations of the fluorescent substance and target substance, which are used in the microarray technique, can appropriately be employed as the concentrations of the fluorescent substance and target substance contained in the sample. Preferably the fluorescent substance is bonded to the target substance. However, the fluorescent substance may be one that bonds to the probe substance and the target substance when the probe substance and the target substance interacted with each other.

When single-stranded DNA is used as the probe substance and the target substance, fluorescent functional groups such as Cy3 and Cy5 can be bonded to a 5' terminal of the target DNA, or allowed to enter the target DNA. cDNA may be labeled by biotin. On the other hand, the interaction of the probe substance and the target substance can also be detected using an intercalater molecule such as POPO-3 (Molecular Probes, Inc.) that adheres specifically to double-stranded DNA to generate fluorescence.

Publicly known solvent, buffer, and pH adjuster may appropriately be contained in the sample in addition to the fluorescent substance and the target substance.

1.4 Sample Chamber

The sample chamber is a part for accommodating the substrate 2, to which the probe substance 1 is fixed, and the probe substance 1, and also accommodating the sample 5 containing the fluorescent substance 3 and the target substance 4 so that the sample 5 is brought into contact with the probe substance 1. A publicly known sample chamber used in the microarray technique can also appropriately be employed for the sample chamber. A preferable sample chamber is a so-called flow-through cell in which the sample flows continuously. Therefore, the sample chamber preferably includes a connecting pipe connecting the sample chamber and a sample storage in which the sample is stored. Preferably the sample chamber also includes a control unit that controls an amount of the buffer solution mixed with the sample, so that a flow rate of the sample flowing in the sample chamber can be controlled. The sample chamber preferably includes a drain pipe to drain the sample from the sample chamber.

In the case where the flow-through cell is used, the target substance contained in the sample is sequentially bonded to the probe substance fixed to the substrate, which causes the problem that the concentration of the target substance is lower in the downstream region than in the upstream region. Because the concentration of the target substance is different between the downstream region and the upstream region, the interaction between the target substance and the probe substance cannot be measured under homogeneous conditions. Therefore, in a preferred embodiment of the invention, one or more connecting pipes connecting the sample storage in which the sample is stored and the sample chamber are connected to a midstream region of the sample chamber in addition to the uppermost-stream region thereof. This allows the difference in the concentration of the target substance between the upstream and downstream regions to be reduced though a large amount of sample will be required.

The sample chamber preferably includes a temperature adjusting unit to adjust a sample temperature. There is no particular limitation to the temperature adjusting unit as long as the temperature adjusting unit can adjust the temperature of the sample solution existing on the microarray substrate, and a publicly known temperature adjusting device can appropriately be employed. For example, the temperature adjusting unit includes a ceramic heater, a thermo-couple temperature sensor, and a heater control unit, the heater control unit performing PID control to the heater and the sensor. For example, when the observation is performed with the DNA microarray, the temperature adjusting unit can maintain the temperature of at least the sample existing in a surface region of the microarray substrate (preferably the whole sample in the sample chamber) at about 65° C. that is a temperature suitable to the hybridization. Since the sample temperature is thus controlled, the state of the hybridization can effectively be measured.

1.5 Optical System

The optical system includes one or more optical elements, and guides the light from the light source 7 to the substrate 2 to generate the evanescent field. Specifically, for example, in the optical system, the light incident on a reflecting plane is parallel to an optical axis of an objective lens 14, and the light is controlled so as to be located at a constant distance from the optical axis. In such case, the light incident on the reflecting plane is reflected to the objective lens 14 so as to be parallel to the optical axis of the objective lens 14 and be offset from the optical axis by the constant distance. Because the optical system 8 of the invention includes the incidence angle adjusting means 10 that adjusts an incidence angle when the light from the light source 7 is incident on the substrate, the incidence angle can be adjusted when the light is incident on the substrate. Therefore, the penetration depth of the evanescent field can be controlled. In such case, in order to generate the evanescent field, preferably the incidence angle adjusting means 10 performs the control such that the incidence angle is larger than a so-called critical angle.

A publicly known light source used in the microarray technique can appropriately be employed as the light source 7. A specific example of the light source may be a continuous laser beam source. There is no particular limitation to the type, wavelength, and light intensity of the laser beam source as long as the fluorescence can be excited by the generated evanescent field. Specific examples of the laser beam source include a Nd:YAG laser, a He—Ne laser, a LED, and a mercury lamp.

A preferred embodiment of the first aspect of the invention relates to the above-described fluorescence reading apparatus 12 in which the optical system 8 includes an optical element 13 on which the light is incident from the light source 7 and an objective lens 14 on which the light transmitted through the optical element 13 is incident, and the incidence angle adjusting means 10 includes an optical element moving means that moves the optical element 13 such that a position thereof relative to the objective lens 14 is changed.

In the embodiment, because the fluorescence reading apparatus includes the optical element moving means, the position of the light incident on the objective lens 14 can be adjusted, by moving the optical element 13 away from the objective lens 14 in a constant direction or by bringing the optical element 13 close to the objective lens 14 in a constant direction, for example. Therefore, the incidence angle of the outgoing light from the objective lens 14 with respect to the substrate surface can be changed, so that the penetration depth of the evanescent field can also be controlled.

Figure 3:
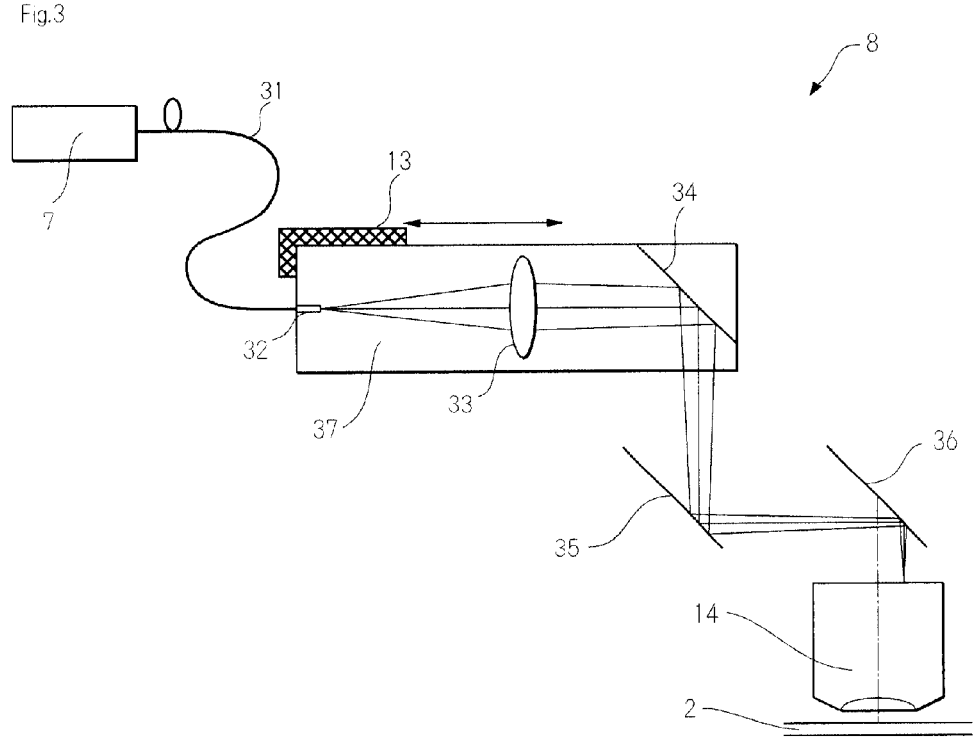
FIG. 3 illustrates an example of an optical system of the invention.

FIG. 3 illustrates an example of the optical system of the invention. Referring to FIG. 3, the example optical system includes an optical fiber 31 into which the light is fed from the light source 7, an outgoing end 32 of the optical fiber 31, a first lens 33 that collects the light incident from the outgoing end 32, and mirrors 34, 35, and 36 that are optional elements for guiding the light emitted from the first lens 33 to the objective lens 14. One or both of the first lens 33 and the first mirror 34 are mounted on a moving stage 37. The optical element moving means 13 is provided on the moving stage 37. A specific example of the optical element moving means 13 may be an actuator attached to the moving stage 37. The moving stage 37 is moved by the actuator in a traveling direction of the light emitted from the outgoing end 32 of the optical fiber 31 or in an opposite direction to the light traveling direction. The controller 11, for example, may control a moving amount of the moving stage by the actuator. Preferably the controller can obtain the incidence angle to the substrate from the moving amount of the moving stage. For example, a focal position can be deviated by moving the first lens, and thus an emission angle of the outgoing light from the objective lens can be controlled. When the first lens is moved, an optical path length is changed to deviate the focal position, so that the emission angle of the outgoing light from the objective lens can be controlled. In FIG. 3, the numeral 38 designates oil.

There is no particular limitation to the first lens 33 as long as the first lens can collect the laser beam. A publicly known lens can appropriately be employed as the first lens. For example, instead of moving the actuator, the focal position can also be deviated by controlling an angle of one or more of the mirrors 34, 35, and 36. In the technique of controlling the angle of the mirror, a mass of the movable unit can be reduced compared with the technique of moving the optical system. Therefore, scanning can be performed at high speed.

The objective lens 14 is an optical element that acts as a lens that collects the fluorescence gene rated on the substrate 2. In a preferred embodiment of the invention, the objective lens 14 causes the light emitted from the light source 7 to be incident on the substrate 2 such that the evanescent field is generated in the surface of the substrate 2 to which the probe substance is fixed. A publicly known objective lens used in the microarray apparatus can appropriately be employed as the objective lens. The sectional shape of the prism may appropriately be polygonal, semi-circle, and fan-like other than triangle.

Preferably an oil layer is provided between the objective lens 14 and the substrate 2. The oil layer can match a refractive index of the objective lens 14 with a refractive index of the substrate 2. Therefore, the reflection of the light can be reduced at the boundary surface between the objective lens and the substrate. Further, the evanescent field can effectively be generated in the surface of the microarray substrate, and the fluorescence can efficiently be collected from a specimen. Publicly known oil (refractive index matching oil) used in the microarray detecting apparatus can appropriately be employed as the oil constituting the oil layer.

Figure 4:
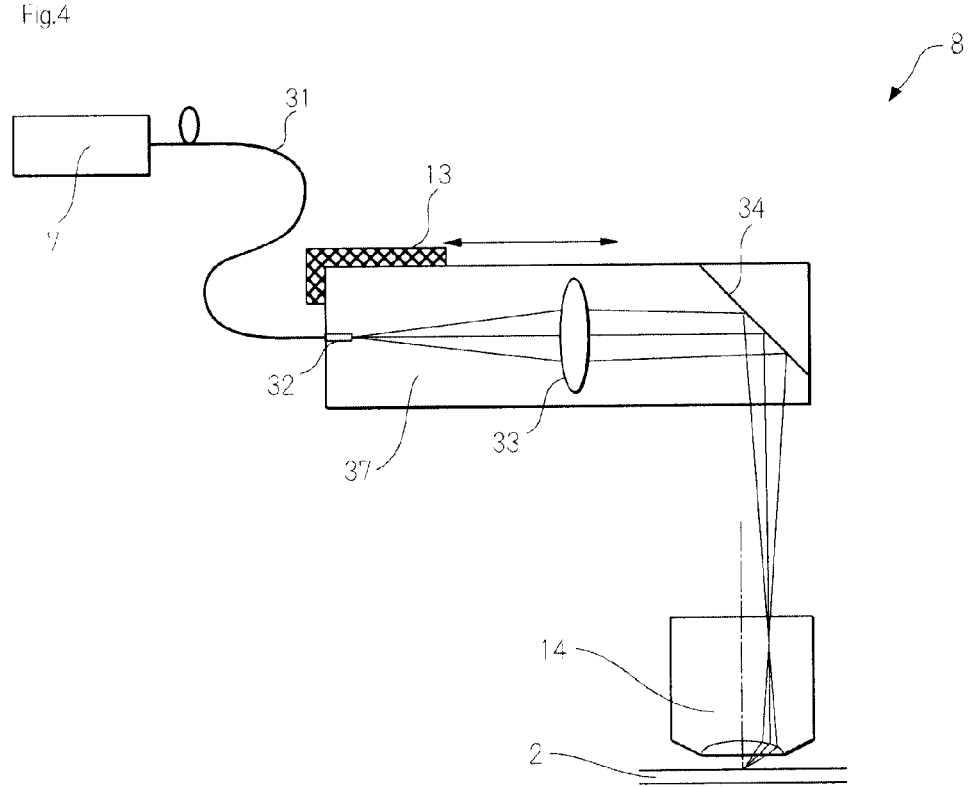
FIG. 4 illustrates an example of the optical system of the invention different from that illustrated in FIG. 3.

FIG. 4 illustrates an example of the optical system of the invention different from that illustrated in FIG. 3. Referring to FIG. 4, the example optical system includes the optical fiber 31 into which the light is fed from the light source 7, the outgoing end 32 of the optical fiber 31, the first lens 33 that collects the light incident from the outgoing end 32, and the first mirror 34 that is an optional element for guiding the light emitted from the first lens 33 to the objective lens 14. One or both of the first lens 33 and the first mirror 34 are mounted on the moving stage 37. The optical element moving means 13 is provided on the moving stage 37. That is, the mirror is for adjusting the optical path, and more mirrors may be provided, or the mirror may not be provided. The first mirror may not be provided, in which case, the outgoing end 32 of the optical fiber 31, the first lens 33 and the objective lens 14 may be disposed in the same straight line, for example.

Figure 5:
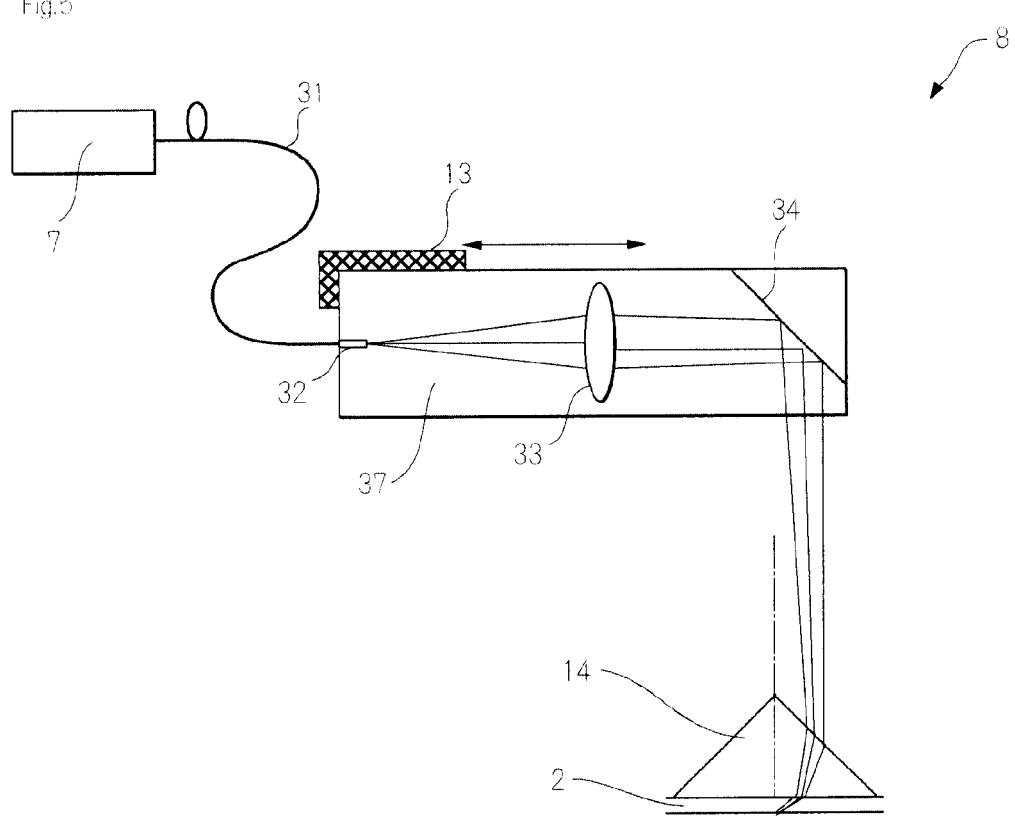
FIG. 5 illustrates an example of the optical system of the invention different from those illustrated in FIGS. 3 and 4.

FIG. 5 illustrates still another example of the optical system of the invention different from those illustrated in FIGS. 3 and 4. Referring to FIG. 5, the optical system that generates the evanescent field may be provided independently from the objective lens, in which case the triangular prism or the like is appropriately used such that the irradiation light is incident at an angle that is equal to or more than a total reflection angle, and the objective lens is disposed to detect the fluorescence (see FIG. 5). In the case where the optical system independent from the objective lens is used, because a numerical aperture of the objective lens can be decreased to 1.33 or less, the design flexibility of the optical system can be enhanced, and the optical system can be designed at low cost. When the irradiation light is given through the objective lens, the number of components included in the optical system can be decreased, and the need for aligning the irradiation light and the observation region is eliminated. Further, by employing the objective lens having high numerical aperture, the fluorescence from the observation region can more efficiently be received.

In a preferred embodiment of the invention, the fluorescence reading apparatus includes a plurality of objective lenses and an optical system that guides the light to the plurality of objective lenses. In the fluorescence reading apparatus, for example, two or more optical systems as described above are provided, or the light from the light source is appropriately divided to provide a plurality of light irradiation systems, which allows a plurality of spots on one substrate to be simultaneously observed. Each objective lens generates the evanescent field in the spot provided in the substrate 2. That is, in the real-time microarray reading apparatus in which the flow-through cell is used, one of the advantages is that the temporal change in fluorescence intensity in a plurality of spots can also be observed. However, because one spot can be measured at a time, there is a problem that a time lag is generated in measuring a plurality of spots. In a preferred embodiment of the invention, a plurality of spots can be simultaneously measured, so that the temporal changes of the plurality of spots at the same time can properly be observed. In order to ensure the operating range of the optical system, addressing such needs, preferably a spot interval in the substrate is larger than typical one (for example, a center distance between spots ranges from 50 µm to 200 µm). Specifically, a plurality of sets of the light source 7, the optical system 8, and the fluorescence detector 9 of FIG. 1 are prepared, and each objective lens 14 is located in the different spot of the substrate 2. Therefore, the plurality of spots can simultaneously be observed. Alternatively, the light from the light source 7 may be divided by a light dividing means such as a beam splitter to assemble an optical system, the plurality of objective lenses 14 facing the substrate 2 may be prepared, and each light divided by the beam splitter, etc., may be guided to each objective lens 14. In such case, preferably the fluorescence detector 9 corresponding to each objective lens is provided, and the controller such as the computer 11 performs a predetermined operation on the outputs from all the fluorescence detectors 9. Alternatively, the objective lense corresponding to each side of the substrate 2 may be disposed, and a plurality of optical fibers may be provided to guide the light to the objective lenses, thereby guiding a plurality of exciting light beams to the plurality of spots. Alternatively, a plurality of light beams may be guided to the substrate 2 such that the evanescent field is generated in the plurality of spots without use of the objective lens.

1.6 Fluorescence Detector

The fluorescence detector is a device that detects the fluorescence intensity or fluorescence image, which is generated by the fluorescent substance excited by the evanescent field. A publicly known fluorescence detector used in the microarray technique can appropriately be employed as the fluorescence detector 9.

Figure 6:
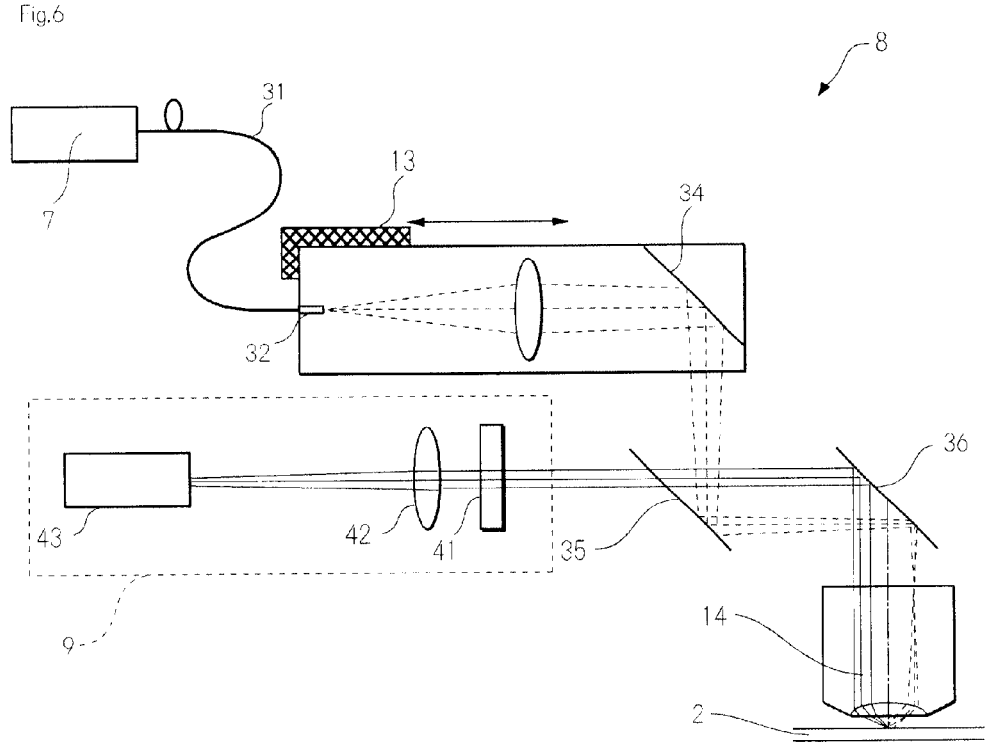
FIG. 6 illustrates an example of a fluorescence detector.

FIG. 6 illustrates an example of the fluorescence detector. As illustrated in FIG. 6, the fluorescence detector 9, for example, includes an optical filter 41, an imaging lens 42, and a photodetector 43. The optical filter 41 transmits the fluorescence generated by the fluorescent substance, and reduces the exciting light to reduce noise. The imaging lens 42 forms an image of the fluorescence transmitted through the optical filter. The photodetector 43 detects the light passing through the imaging lens. Particularly, the optical filter is optional and may not be provided. Any optical filter that reduces the intensity of the light in a wavelength range including the exciting light may be used. A photodetector used in a publicly known optical instrument can appropriately be employed as the photodetector. Specific examples of the photodetector include a photodiode and a CCD camera such as a cooling CCD camera. When the photodiode is used as the photodetector, the fluorescence intensity of the observation point as a whole can be detected. The CCD camera is preferably used because the fluorescence intensity can be obtained in each pixel constituting a CCD, thereby obtaining the fluorescence image.

1.7 Controller

The controller 11 is a device that controls the amount of incidence angle adjusted by the incidence angle adjusting means 10. For example, in the case where the incidence angle adjusting means 10 changes the position of an optical element such as a mirror, the position of the optical element is changed based on a predetermined control instruction, which allows the amount of incidence angle to be controlled. Further, preferably the controller stores a relationship between the position of the optical element and the incidence angle, so that the position of the optical element is controlled and the incidence angle of the incident light is obtained. In addition, preferably the controller also stores a relationship between the incidence angle and the penetration depth of the evanescent field, so that the information on the penetration depth of the evanescent field is obtained from the information on the incidence angle.

A preferred embodiment of the first aspect of the invention relates to any of the above-described fluorescence reading apparatus 12, in which the controller includes a means for receiving information on the incidence angle adjusted by the incidence angle adjusting means 10 and information on the fluorescence intensities or fluorescence images at a plurality of incidence angles detected by the fluorescence detecting unit 9 and obtaining the penetration depths of the evanescent fields with respect to the plurality of incidence angles from the information on the incidence angles; and a means for obtaining information on the fluorescence intensities in the obtained plurality of penetration depths. In the fluorescence reading apparatus of the embodiment, by adjusting the incidence angle, the information on the fluorescence intensities in the plurality of penetration depths can be obtained while the penetration depth of the evanescent field is controlled.

Specifically, a computer in which "a program for causing the computer to act as a means for receiving the information on the incidence angle adjusted by the incidence angle adjusting means 10 and the information on the fluorescence intensities at a plurality of incidence angles detected by the fluorescence detecting unit 9 to obtain the penetration depths of the evanescent fields with respect to the plurality of incidence angles from the information on the incidence angles and obtaining the information on the fluorescence intensities in the plurality of obtained penetration depths, and thereby obtaining the relationship between the penetration depths of the evanescent fields and the fluorescence intensities with respect to the plurality of penetration depths" is installed may be used.

There is known a predetermined relationship between the incidence angle and the penetration depth of the evanescent field. Therefore, a coefficient and a predetermined operation program may be previously stored, so that, when the information on the incidence angle is fed, the coefficient is read and the operation program is executed to obtain the penetration depth of the evanescent field. That is, the controller includes an input means, a coefficient storage means, an operation means, a penetration depth storage means, and an output means. The input means is fed with information on the incidence angle. The coefficient storage means stores predetermined coefficient information in a relational expression of the incidence angle and the evanescent field. When the information on the incidence angle is fed into the input means, the operation means reads the coefficient information stored in the coefficient storage means and performs an operation to obtain the penetration depth of the evanescent field using the fed information on the incidence angle. The penetration depth storage means stores the information on the penetration depth of the evanescent field obtained by the operation means. The output means outputs the information on the penetration depth of the evanescent field, which is stored in the penetration depth storage means. The controller includes a table in which a predetermined penetration depth is stored in association with each incidence angle. And when the information on the incidence angle is fed, the information on the penetration depth may be read based on the information on the incidence angle.

Thus, a predetermined penetration depth is obtained, the incidence angle (that is, the position of the optical element) that gives the penetration depth and the fluorescence intensity at that time are fed into the controller, so that the fluorescence intensity in a given penetration depth can be observed. The controller includes the input unit, the control unit, the operation unit, the storage unit, and the output unit, and the respective units are connected to one another through a bus or the like to exchange information. The storage unit stores various values, tables, control programs and the like. When predetermined information is fed from the input unit into the control unit, the control unit may perform a predetermined operation using various information stored in the storage unit, store the operation results in the storage unit, and appropriately output the operation results from the output unit. When predetermined information is fed from the input unit into the control unit, the control unit may read the control programs stored in the storage unit such as a main memory based on the fed information, read various information from the storage unit according to instructions from the control programs, perform various operation processing using the operation unit, store the operation results in the storage unit, and appropriately output the operation results from the output unit.

A preferred embodiment of the first aspect of the invention relates to any of the above-described fluorescence reading apparatus 12, in which the controller includes a means for obtaining a graph, using relationships between the penetration depths of the evanescent fields and the fluorescence intensities with respect to the plurality of penetration depths, in which one of axes (for example, vertical axis) represents the fluorescence intensity while the other axis (for example, horizontal axis) represents the penetration depth of the evanescent field. The controller includes the means for obtaining the graph, using the relationships between the penetration depths of the evanescent fields and the fluorescence intensities with respect to the plurality of penetration depths, in which one of the axes represents the fluorescence intensity while the other axis represents the penetration depth of the evanescent field. "The relationship between the penetration depth of an evanescent field and the fluorescence intensity" refers to a penetration depth d of the evanescent field and a value of the fluorescence intensity in the penetration depth d.

In the embodiment, the fluorescence reading apparatus supplies the information on the obtained graph to a display device such as a monitor, and the graph is displayed on the display device. According to the fluorescence reading apparatus of the embodiment, the graph in which one of the axes represents the fluorescence intensity while the other axis represents the penetration depth of the evanescent field can be displayed using the relationships between the penetration depths of the evanescent fields and the fluorescence intensities with respect to the plurality of penetration depths, so that the determination whether the observed fluorescence includes only noise fluorescence can readily visually be made. That is, a user refers to the graph to estimate the state in which each observation point is plotted. When only the noise fluorescence is observed, an intercept when the penetration depth is zero becomes equal to or less than a threshold. Therefore, according to the fluorescence reading apparatus of the embodiment, the influence of the noise fluorescence can be considered.

FIG. 7 is an example of a graph showing observation data at a certain observation point, in which a vertical axis represents the fluorescence intensity while a horizontal axis represents the penetration depth of an evanescent field. FIG. 7A shows raw observation data, and FIG. 7B is a graph in which the observation data is plotted. In FIGS. 7A and 7B, triangles, cross symbols, and circles respectively indicate observation values at different observation points. Each point is the information indicating "the relationship between the penetration depth of the evanescent field and the fluorescence intensity". The graph of FIG. 7A is an example of the "graph in which the vertical axis represents the fluorescence intensity while the horizontal axis represents the penetration depth of the evanescent field".

In the embodiment, the fluorescence reading apparatus, for example, outputs the information on the obtained graph to a display device such as a monitor, and the graph is displayed on the display device. That is, according to the fluorescence reading apparatus of the embodiment, the graph in which one of the axes represents the fluorescence intensity while the other axis represents the penetration depth of the evanescent field can be displayed using the relationships between the penetration depths of the evanescent fields and the fluorescence intensities with respect to the plurality of penetration depths, so that the determination whether the observed fluorescence is the noise fluorescence can readily visually be made.

FIG. 7B is a conceptual graph showing the state in which the graph of FIG. 7A is visually plotted. That is, the user refers to the graph to estimate the state in which each observation point is plotted. when only the noise fluorescence is observed, the intercept when the penetration depth is zero becomes equal to or less than the threshold. Therefore, according to the fluorescence reading apparatus of the embodiment, the influence of the noise fluorescence can be considered. Specifically, because the line connecting the circular marks shows that the intercept exceeds the threshold although the fluorescence intensity is generally low, it can be deemed that the probe substance and the target substance have interacted with each other.

A preferred embodiment of the first aspect of the invention relates to any of the above-described fluorescence reading apparatus 12, in which the controller includes a means for obtaining a graph, using relationships between the penetration depths of the evanescent fields and the fluorescence intensities with respect to a plurality of penetration depths, in which one of axes represents the fluorescence intensity while the other axis represents the penetration depth of the evanescent field; a means for obtaining a hypothetical fluorescence intensity using each point on the graph when the penetration depth of the evanescent field is zero; a means for comparing a set threshold and the hypothetical fluorescence intensity when the penetration depth of the evanescent field is zero; and a means for determining whether the probe substance 1 and the target substance 4 have interacted with each other using the comparison result.

Specifically, a computer in which "a program for causing the computer to act as a means for obtaining the graph, using the relationships between the penetration depths of the evanescent fields and the fluorescence intensities with respect to a plurality of penetration depths, in which one of the axes represents the fluorescence intensity while the other axis represents the penetration depth of the evanescent field; a means for obtaining the hypothetical fluorescence intensity using each point on the graph when the penetration depth of the evanescent field is zero; a means for comparing the set threshold and the hypothetical fluorescence intensity when the penetration depth of the evanescent field is zero; and a means for determining whether the probe substance 1 and the target substance 4 have interacted with each other using the comparison result" is installed may be used as the controller.

"A means for obtaining the hypothetical fluorescence intensity using each point on the graph when the penetration depth of the evanescent field is zero" is a means for performing plotting for each observation point shown in FIG. 7A as shown in FIG. 7B. Various methods of plotting the observation points on the graph are known, and a publicly known method can appropriately be employed. By the simplest plotting method, the observation points adjacent to each other are simply connected. Regarding the end point, a straight line connecting the end point and the adjacent observation point may be extended, for example. Then, the fluorescence intensity at the intersection point of the vertical axis and the line in which each observation point is plotted, that is, at the point where the penetration depth is zero, may be obtained.

"A means for comparing the set threshold and the hypothetical fluorescence intensity when the penetration depth of the evanescent field is zero" is a means for reading the threshold stored in the storage unit and comparing "the hypothetical fluorescence when the penetration depth of the evanescent field is zero" obtained in the previous process with the threshold. The comparison of the values can easily be performed using a comparison circuit. For example, "1" may be output when the former is larger than the latter, and "0" may be output when the latter is equal to or larger than the former.

"A means for determining whether the probe substance 1 and the target substance 4 have interacted with each other using the comparison result" is, for example, a means for determining that the probe substance and the target substance have interacted with each other when "the hypothetical fluorescence intensity when the penetration depth of the evanescent field is zero" is larger than the threshold. Specifically, when the "1" is received, it is determined that the probe substance and the target substance have interacted with each other, while, when the "0" is received, it is determined that the probe substance and the target substance have not interacted with each other. In such cases, the display signal corresponding to the "1" or "0" may be read and output. Therefore, the information indicating the presence or absence of the interaction will be displayed on the monitor, etc.

The fluorescence reading apparatus 12 of the embodiment can automatically determine whether the probe substance and the target substance have interacted with each other. A criterion for the determination can appropriately be changed by modifying the set threshold.

A preferred embodiment of the first aspect of the invention relates to any of the above-described fluorescence reading apparatus 12, in which the controller includes a means for observing elapsed time.

Specifically, the microarray or the like rapidly detects the fluorescence from a plurality of spots. If time information when fluorescence is detected from a certain spot is stored, the fluorescence intensity of the spot can be observed at a plurality of times when the fluorescence of the spot is detected again later. Accordingly, the temporal change in fluorescence intensity of the spot can be observed. Therefore, the final interaction amount can be predicted while how the interaction such as the hybridization proceeds can be observed. That is, in a preferred embodiment of the invention, the fluorescence reading apparatus includes a means for obtaining a relationship between a fluorescence intensity at a certain observation point or at the intercept and time. With this, the temporal change in fluorescence intensity at a certain spot can be observed. Therefore, according to the invention, the fluorescence reading apparatus that can perform real-time observation can be provided. In a preferred embodiment of the invention, the fluorescence reading apparatus includes a means for obtaining a change in fluorescence intensity after a predetermined time elapses; and a means for comparing the change in fluorescence intensity and a threshold, wherein the latest fluorescence intensity when the change in fluorescence intensity is equal to or less than the threshold is set to the final fluorescence intensity. Therefore, the final fluorescence intensity can rapidly be predicted. The threshold may be a constant value, or may be a value ranging from one-third to a half of the immediately preceding change in fluorescence intensity.

Japanese Patent Application Laid-Open No. 2006-38816 describes the state of the hybridization of the target DNA and the probe DNA. Assuming that the target DNA and the probe DNA are hybridized and X is the number of molecules of the target DNA fixed to the microarray substrate surface, the number of molecules X is expressed as follows:

$$X=C(1-\exp(-t/\alpha)),$$

where C is the number of molecules of the target DNA contained in the specimen, $\alpha$ is a constant determined from a ratio of a reaction rate and a desorption rate when the hybridization reaction occurs, and t is a detection time.

That is, in the invention, because the temporal change in fluorescence intensity can also be obtained, the value $\alpha$ and the value C can be obtained by fitting the information on the fluorescence intensities detected at a plurality of times in the above equation.

A preferred embodiment of the first aspect of the invention relates to any of the above-described fluorescence reading apparatus 12, in which the substrate includes at least 10, preferably at least 30, more preferably at least 100, and most preferably at least 300 spots 21 to which the probe substance is fixed, the fluorescence detecting unit 9 obtains the fluorescence image generated by the fluorescent substance 3, and the controller 11 includes a means for scanning the fluorescence image to compute a boundary 21 at which the fluorescence intensity is changed; a means for grasping a region 23 inside the spot and a region 24 outside the spot in the fluorescence image based on a shape of the boundary; and a means for obtaining the fluorescence intensity inside the spot. Preferably a plurality of spots 21 are provided in the substrate 2.

FIGS. 8A and 8B illustrates an example of an observed fluorescence image, in which FIG. 8A is a photograph in place of a drawing illustrating an example of the observed fluorescence image, and FIG. 8B illustrates a boundary obtained using the image of FIG. 8A, the fluorescence intensity being changed at the boundary. In FIG. 8, the numeral 21 designates a spot, the numeral 22 designates a boundary, the numeral 23 designates a region where the fluorescence from the inside of the spot is observed, and the numeral 24 designates a region where the fluorescence from the outside of the spot is observed.

As illustrated in FIG. 8, generally, when a fluorescence image of a certain spot is obtained, the fluorescence image may include both the inside of the spot 21 and the outside of the spot 21. In such case, the fluorescence 24 from the outside of the spot may be higher than the fluorescence 23 from the inside of the spot in intensity. On the other hand, because the probe substance is not fixed to the outside of the spot, the fluorescence from the outside of the spot is deemed to be a noise component. Accordingly, when the fluorescence intensity is directly analyzed from the fluorescence image, the interaction between the probe substance and the target substance cannot correctly be grasped. According to the fluorescence reading apparatus 12 of the embodiment, the boundary 22 between the inside of the spot and the outside of the spot is grasped from the fluorescence image, and then the fluorescence intensity inside the spot is obtained, so that the interaction can be grasped more accurately than in a conventional art.

A publicly known means used in bioaffymetrics such as OCR, OMR, fingerprint recognition, and vein recognition can appropriately be employed as "a means for scanning the fluorescence image to compute the boundary at which the fluorescence intensity is changed". Specifically, an operation of scanning the fluorescence intensity distribution in an X-axis direction is repeatedly performed while a Y-axis is changed, and a point at which the fluorescence intensity distribution is changed is obtained. Therefore, the boundary at which the fluorescence intensity is changed can be computed.

"A means for grasping the region inside the spot and the region outside the spot in the fluorescence image based on the shape of the boundary" can use the information on the boundary, for example, because the boundary is obtained in the above process. Specifically, an outer periphery of the spot has a circular shape. Therefore, the inside and outside of the spot can be grasped from each other by obtaining a gradient of the boundary. In the case where the penetration depth of the evanescent field is changed, a portion having a large fluctuation in fluorescence intensity can be the outside of the spot. Therefore, the changes in fluorescence intensity in a plurality of penetration depths with respect to the two regions that are divided by the boundary may be observed to determine that the region having the smaller fluctuation is the inside of the spot.

"A means for obtaining the fluorescence intensity inside the spot" may be, for example, a means for computing a fluorescence intensity per unit area in the spot grasped in the above-described manner. Because the information on the fluorescence intensity of the region corresponding to each pixel is obtained in a CCD camera, the total or average of the fluorescence intensities included in a certain region can easily be obtained by performing addition operation or subtraction operation.

1.8 Substrate Moving Means

A preferred embodiment of the first aspect of the invention relates to any of the above-described fluorescence reading apparatus 12 that includes a substrate moving means 15 that moves a position of the substrate 2. An example of the substrate moving means may be an actuator attached to the substrate. The substrate is moved by the actuator in longitudinal and crosswise directions in a plane that is parallel to the surface of the objective lens 14, so that the evanescent field can be moved to each spot provided in the micro substrate. In order to perform the detection, positional information on each spot in the substrate is stored in the storage unit of the controller 11, and the controller 11 controls the moving amount of a moving stage moved by the actuator. That is, a plurality of spots are provided in the microarray, and various kinds of probe substances are fixed to each spot. In the embodiment, because the fluorescence reading apparatus includes the substrate moving means 15, the substrate 2 can be moved such that the evanescent field is generated in each spot. Therefore, fluorescence intensities of various probe substances can be observed.

1.9 Autofocus Maintaining Mechanism

The fluorescence reading apparatus of the invention may include an autofocus maintaining mechanism that keeps a distance between the objective lens and the substrate constant. By including the autofocus maintaining mechanism, the fluorescence reading apparatus can measure the distance between the objective lens and the substrate using a component that is reflected and returned from the substrate in the irradiation light generating the evanescent field. Because the light returned from the objective lens is reflected by a dichroic mirror 35, the reflected light can be taken out upward when a partially transparent mirror is used as the mirror 34. For example, the light is collected onto a CCD 43 by a lens 40, and the collective spot position is monitored. When the distance between the objective lens and the substrate is changed, the collective spot is moved in the crosswise direction. Accordingly, by adjusting the vertical position of the objective lens by the moving mechanism such that the collective spot position is kept constant, the focal point can be maintained. In order to automate the focus maintaining device, the image obtained from the CCD 43 is captured in the computer, the collective spot position is detected by image processing, and a signal for controlling the moving mechanism is supplied such that the collective spot position is kept constant. When the autofocus maintaining mechanism is incorporated in the fluorescence reading apparatus, the progress of the bonding reaction for a long time can stably be observed. The substrate and the solution is desirably heated to a temperature of about 50° C. in observing the progress of the hybridization, which causes a problem that the focal point is deviated by the temperature change. However, the influence can be reduced by incorporating the autofocus maintaining mechanism in the fluorescence reading apparatus.

1.10 Multiple Simultaneous Measuring System

A typical real-time microarray measuring apparatus includes one sample chamber. In such case, only one spot can be measured at a time, which causes a problem that the states of a plurality of spots at the same time cannot correctly be observed. Therefore, a preferred embodiment of the invention relates to the fluorescence reading apparatus that includes a sample storage in which the target substance is contained; and a connecting pipe that connects the sample storage and a plurality of sample chambers, wherein the connecting pipe has a branch portion, and downstream portions of each connecting pipe branched by the branch portion of the connecting pipe are connected to the plurality of sample chambers. For each sample chamber, a corresponding light source 7, an optical system 8, and a fluorescence detector 9 are provided, so that a plurality of spots of the sample can easily be observed at the same time.

2.1 Microarray Detection Principle

Figure 9:
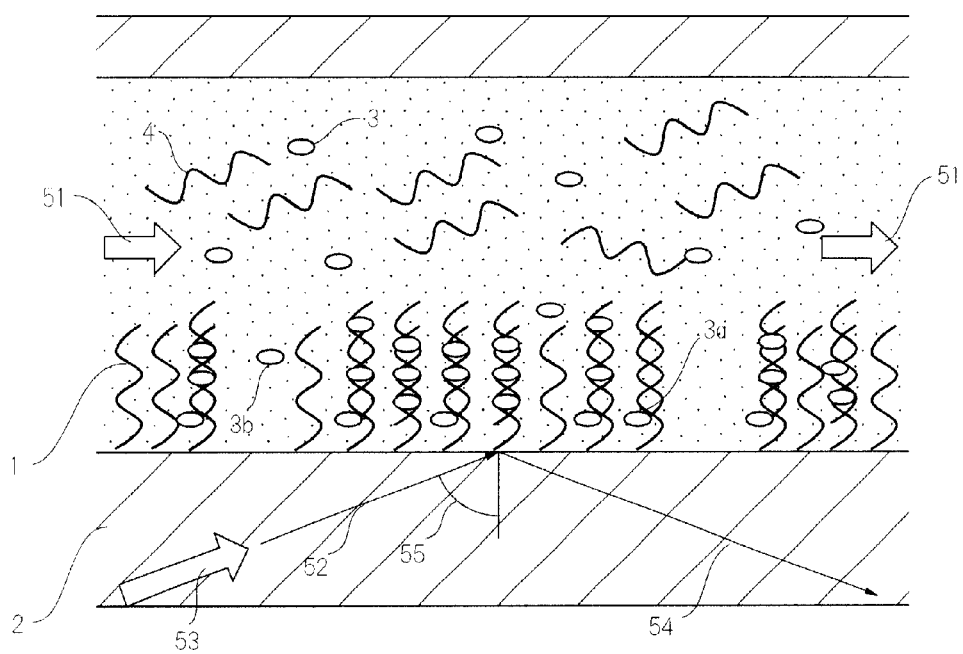
FIG. 9 is a conceptual diagram for explaining a microarray detection principle.

Next, a microarray detection principle will be described. FIG. 9 is a conceptual diagram for explaining a microarray detection principle. As illustrated in FIG. 9, the probe substance 1 is fixed to the substrate 2. The sample including the fluorescent substance 3 and target substance 4 flows in the sample chamber. The arrow 51 indicates the direction in which the sample flows in the sample chamber. In the microarray detecting device of FIG. 9, an incident light 52 from the optical system is incident on the substrate. The arrow 53 indicates a traveling direction of the incident light. The incident light is reflected at the boundary between the substrate and the sample chamber. The numeral 54 designates the reflected light, and the numeral 55 designates the incidence angle.

When predetermined conditions are satisfied, the evanescent field is generated under the above-described conditions. The fluorescent substance 3 is then excited by the evanescent field to generate the fluorescence. The excited fluorescent substance includes a fluorescent substance 3b that is not involved with the interaction between the probe substance and the target substance in addition to a fluorescent substance 3a involved with the interaction between the probe substance and the target substance.

2.2 Relationship between Incidence Angle and Penetration Depth of Evanescent Field As described, for example, in Japanese Patent Application Laid-Open No. 10-2836, the following relationship is between the incidence angle and the penetration depth of the evanescent field.

[Formula 1]

$$D_0 \approx \frac{\lambda}{2\pi\sqrt{n_g^2 \times \sin^2\theta - n_L^2}}$$

$D_0$ is a penetration depth (μm) of the evanescent field, $\lambda$ is a wavelength of the incident light, and $\theta$ is an incidence angle of the light incident on the substrate, $n_g$ is a refractive index of a lower substrate, and $n_L$ is a refractive index of a liquid crystal (or oriented film). Although the optically anisotropy measuring apparatus disclosed in Japanese Patent Application Laid-Open No. 10-2836 differs from the fluorescence reading apparatus of the invention in the shape of the objective lens, the observation target and the like, the principle of the generation of a evanescent field is the same in both cases. That is, in the system of the invention, the penetration depth of the evanescent field is changed depending on the incidence angle of the incident light.

2.3 Relationship between Penetration Depth of Evanescent Field and Fluorescence Intensity In the case where the probe substance and the target substance are hybridized, the fluorescent substance fixed to the substrate by the hybridization is affected by the evanescent field to generate the fluorescence. In the DNA microarray apparatus, the interaction between the probe substance and the target substance is observed by observing the fluorescence generated by the hybridization. However, in the real-time observation type DNA microarray apparatus, the fluorescence derived from the fluorescent substance flowing in the portion distant from the substrate is also observed in addition to the fluorescence involved with the hybridization. Desirably the fluorescence derived from the fluorescent substance that is not fixed to the substrate is removed because the fluorescence is not generated by the hybridization.

In a conventional real-time observation type DNA microarray apparatus, the fluorescence derived from the fluorescent substance that is not fixed to the substrate may be stronger than the fluorescence derived from the hybridization, which is intended to be observed.

In the DNA microarray apparatus of the invention, the probe substance and the target substance are hybridized, and the fluorescent substance fixed to the substrate is excited by the evanescent field. The interaction between the probe substance and the target substance is evaluated by measuring the intensity of the fluorescence generated by the fluorescent substance excited by the evanescent field.

The intensity of the evanescent field is attenuated in an exponential manner with respect to a distance z from the substrate. The fluorescent substance is excited by the evanescent field with an excitation probability that is proportional to a local light intensity to generate the fluorescence. That is, assuming that $d_i$ is a penetration depth of the evanescent field and $A_0$ is a constant, the local light intensity indicating the excitation probability can be expressed as follows:

[Formula 2]

$$I_i = A_0 \exp\left(-\frac{z}{d_i}\right) \quad (1)$$

On the other hand, it is contemplated that fluorescence $I_i$ detected in the real-time observation type DNA microarray apparatus is the sum of fluorescence $I_{Pi}$ derived from the fluorescent substance that flows in the flow-through cell and is not fixed to the substrate and fluorescence $I_{Qi}$ derived from the fluorescent substance that is fixed to the substrate by the hybridization of the probe substance and the target substance. Therefore, a relationship among the observed fluorescence $I_i$, the fluorescence $I_{Pi}$ that is the noise component, and the fluorescence $I_{Qi}$ that is the observation target can be expressed as follows:

[Formula 3]

$$I_i = I_{Pi} + I_{Qi} \quad (2)$$

It is assumed that a fluorescence intensity $I_{Pi}$ derived from the fluorescent substance flowing in the flow-through cell and the fluorescent substance flowing in the flow-through cell are evenly distributed with respect to the distance z. Then, the fluorescence intensity $I_{Pi}$ that is the noise component can be obtained as follows, where P is the concentration of the fluorescent substance:

[Formula 4]

$$I_{Pi} = \int_0^\infty P A_0 \exp\left(-\frac{z}{d_i}\right) dz \quad (3)$$

$$= P A_0 d_i \left[\exp\left(-\frac{z}{d_i}\right)\right]_0^\infty$$

$$= P A_0 d_i \quad (4)$$

Assuming that Q is the number of fluorescent molecules fixed per unit area, the fluorescence $I_{Qi}$ derived from the fluorescent substance fixed to the substrate can be obtained as follows:

[Formula 5]

$$I_{Qi} = Q A_0 \exp\left(-\frac{z}{d_i}\right)\bigg|_{z=0} \quad (5)$$

$$= Q A_0 \quad (6)$$

The relationship among the observed fluorescence $I_i$, the fluorescence intensity $I_{Pi}$ that is the noise component, and the fluorescence $I_{Qi}$ that is the observation target can be expressed by the following equation (7) based on the equations (2), (4), and (6):

[Formula 6]

$$I_i = I_{Pi} + I_{Qi} \\ = PA_0 d_i + QA_0 \qquad (7)$$

As can be seen from the equation (7), because P and A0 are constants while Q is a certain value, the fluorescence intensity is a function of $d_i$. When $d_i$ is set to d for simplicity, the observed fluorescence intensity I(d) can be expressed as follows:

[Formula 7]

$$I(d) = PA_0 d + QA_0 \qquad (8)$$

Figure 10:
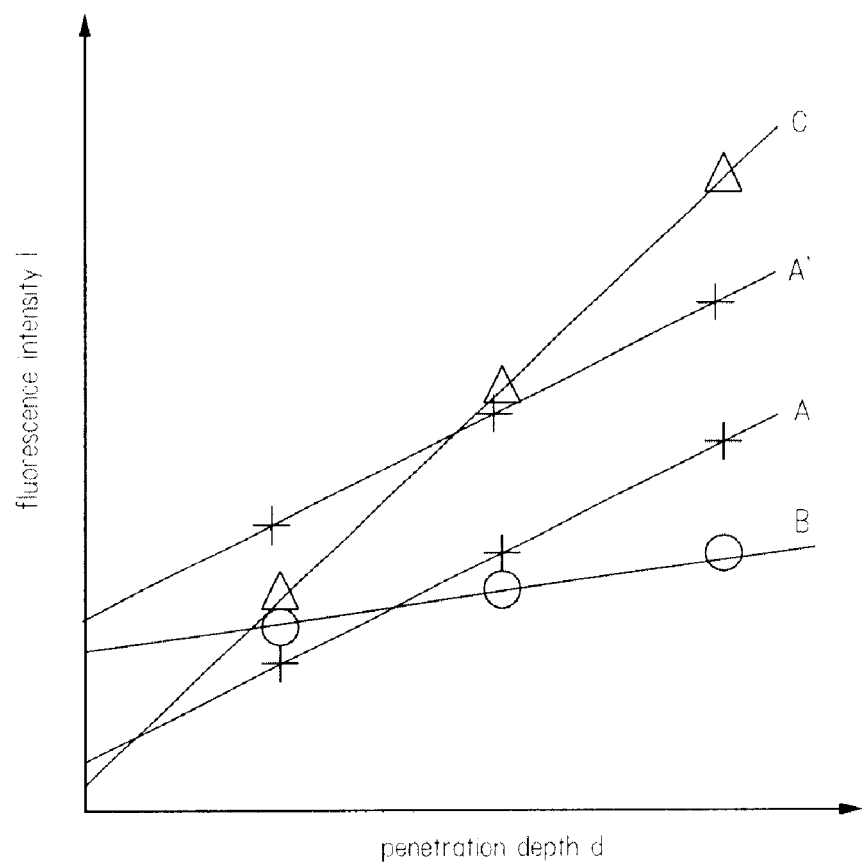
FIG. 10 is a hypothetical graph showing an observation pattern of a real-time observation type DNA microarray apparatus.

An observation pattern of the real-time observation type DNA microarray apparatus is analyzed based on the equation (8). FIG. 10 is a hypothetical graph showing an observation pattern of a real-time observation type DNA microarray apparatus. In FIG. 10, the vertical axis indicates the observed fluorescence intensity (arbitrary unit), and the horizontal axis represents the penetration depth (arbitrary unit) of the evanescent field.

In FIG. 10, the graph A expresses the case in which the fluorescence intensity $I_{Pi}$ derived from the fluorescent substance flowing in the flow-through cell is dominant in the observed fluorescence. That is, in the case where the fluorescence $I_{Qi}$ derived from the fluorescent substance fixed to the substrate does not exist, the fluorescence intensity I(d) becomes zero when d is zero based on the equation (8). That is, in the case where the fluorescence intensity $I_{Pi}$ derived from the fluorescent substance flowing in the flow-through cell is dominant, the y intercept approaches zero when d is brought close to zero. Therefore, when the fluorescence intensities are observed to plot the observation points in some penetration depths of the evanescent fields, the fluorescence intensity $I_{Pi}$ derived from the fluorescent substance flowing in the flow-through cell is dominant if the y intercept is close to zero, and it is contemplated that the probe substance and the target substance have not been hybridized.

Then the graph B is discussed. In a penetration depth of the evanescent field, the fluorescence intensity of the graph A is stronger than the fluorescence intensity of the graph B in some regions. That is, in the conventional real-time observation type DNA microarray apparatus, because the fluorescence intensity is measured in a fixed penetration depth of the evanescent field, the graph A may be presumed to show the hybridization of the probe substance and the target substance while the graph B may be presumed to show that the probe substance and the target substance are not hybridized. However, in the graph B, if the fluorescence intensities are observed in some penetration depths of the evanescent fields and the observation points are plotted, the y intercept does not approach zero. Therefore, in the graph B, it is determined that there is a high probability that the probe substance and the target substance have been hybridized.

Then the graph C is discussed. In the graph C, strong fluorescence intensity is observed in a measuring region of the typical real-time observation type DNA microarray apparatus, and there is a high probability that it is presumed that the probe substance and the target substance are hybridized in common cases. However, in the graph C, if the fluorescence intensities are observed in some penetration depths of the evanescent fields and the observation points are plotted, the y intercept approaches zero. That is, according to the invention, the determination can correctly be made that the probe substance and the target substance have not been hybridized even in the case where the generation of the hybridization is falsely recognized in common cases.

That is, when the fluorescence intensity is measured while the penetration depth of the evanescent field is fixed, it is difficult to determine whether the strong fluorescence intensity is derived from the hybridization of the probe substance and the target substance or a large number of noise components. On the other hand, according to the invention, the determination whether the high fluorescence intensity is derived from a large number of noise components can be made even when the high fluorescence intensity is measured, so that the determination whether the probe substance and the target substance have been hybridized can accurately be made.

Then the graph A' is discussed. The graph A' shows the relationship between some penetration depths of the evanescent fields and the fluorescent intensities in the case where the fluorescence intensities are observed in some penetration depths of the evanescent fields after a while since the state of the graph A and the observation points are plotted. Although the same observation points are observed, the position of the graph is shifted from the graph A to the graph A'. This is attributed to the fact that the hybridization proceed as time has proceeded while the hybridization of the probe substance and the target substance has not proceeded at the time of the observation of the graph A.

That is, the temporal change of the hybridization of the probe substance and the target substance can be grasped by observing the fluorescence intensities at the same positions in some penetration depths of the evanescent fields after an interval, and plotting the observation points. A determination whether the concentration P of the fluorescent substance existing in the flow-through cell can be made by comparing the gradients of the graph A and graph A'. That is, a determination whether the concentration of the fluorescent substance contained in the flow-through cell is kept constant and whether the good condition is maintained can be made by observing the fluorescence intensities at the same positions in some penetration depths of the evanescent fields after an interval, and comparing the gradients of the graphs obtained by plotting the observation points.

3 Operation

An operation of the fluorescence reading apparatus of the invention will be described below. A second aspect of the invention relates to a fluorescence reading method using a fluorescence reading apparatus that detects a specific interaction between a probe substance 1 and a target substance 4, the fluorescence reading apparatus including a substrate 2 to which the probe substance 1 is fixed; a sample chamber 6 that accommodates the probe substance 1 and also accommodates a sample 5 such that the sample 5 is brought into contact with the probe substance 1, the sample containing a fluorescent substance 3 and the target substance 4; a light source 7; an optical system 8 that guides light from the light source 7 to the substrate 2 to generate an evanescent field; and a fluorescence detecting unit 9 that detects a fluorescence intensity or a fluorescence image generated by the fluorescent substance 3 excited by the evanescent field. The fluorescence reading method repeats a step of changing a penetration depth of the evanescent field and a step of obtaining the fluorescence intensity after the penetration depth of the evanescent field is changed, to obtain fluorescence intensities in a plurality of penetration depths of the evanescent field. As illustrated in FIG. 1, the probe substance 1 is fixed to the substrate 2, and the probe substance 1 is brought into contact with the sample 5 in the sample chamber 6. The sample may continuously be supplied. In such case, the controller may appropriately adjust amounts of fluorescent substance 3, target substance 4, buffer, etc., that are contained in the sample, the flow velocity of the sample and the like. When the target substance and the probe substance have behaviors of the hybridization, the target substance and the probe substance are hybridized.

The light emitted from the light source 7 is collected by the collective lens, then reflected by the mirror 13, and guided to the objective lens 14. The light passing through the objective lens is guided to the surface of the substrate 2 to generate the evanescent field. The light reflected from the substrate 2 may be emitted through the objective lens 14 and appropriately observed. In the case where the target substance and the probe substance are hybridized, because the fluorescent substance is fixed to the substrate, the fluorescent substance is excited by the evanescent field generated in the substrate surface to generate the fluorescence.

The generated fluorescence is guided to the fluorescence detecting unit 9 such as a CCD camera through an optical filter that reduces the exciting light and the collective lens that collects the fluorescence. The information on the fluorescence image detected by the fluorescence detecting unit or the fluorescence intensity is transmitted to the controller 11, and the operation processing is appropriately performed.

On the other hand, the controller controls the incidence angle control means to control the incidence angle and obtain the penetration depth of the evanescent field at the controlled incidence angle. Because the penetration depth of the evanescent field can be changed by adjusting the incidence angle of the light incident on the substrate 2, the fluorescence intensities in a plurality of penetration depths of the evanescent fields can easily be obtained. The controller also stores the detection time, spot position, penetration depth, and fluorescence image (or fluorescence intensity) in association with one another. Similar operations are performed for a plurality of incidence angles to obtain the relationship between the penetration depth and the fluorescence intensity. When the fluorescence image is obtained, the fluorescence intensity can be obtained in the above-described manner. Specifically, as illustrated in FIGS. 8A and 8B, the region inside the spot is grasped from the fluorescence image, and the fluorescence intensity is obtained in the fluorescence region inside the spot.

The controller displays the relationship between the penetration depth and the fluorescence intensity as a graph. An example of the display is shown in FIG. 7A. When the graph of FIG. 7A is displayed, the plot of FIG. 7B can be visually recognized, so that the presence or absence of the hybridization can easily be confirmed.

On the other hand, in a preferred embodiment of the invention, the presence or absence of hybridization or the amount of hybridization can be obtained by obtaining the intercept of the graph by actually plotting each observation point, for example, and comparing the obtained value to a threshold. A preferred embodiment of the second aspect of the invention is any of the above-described fluorescence reading method, wherein a graph in which one of axes (for example, vertical axis) represents the fluorescence intensity while the other axis (for example, horizontal axis) represents the penetration depth of the evanescent field is obtained using relationships between the penetration depths of the evanescent fields and the fluorescence intensities with respect to the plurality of penetration depths. Because the graph in which one of the axes represents the fluorescence intensity while the other axis represents the penetration depth of the evanescent field can be displayed using the relationships between the penetration depths of the evanescent fields and the fluorescence intensities with respect to the plurality of penetration depths, the determination whether the observed fluorescence includes only the noise fluorescence can readily visually be made. That is, the user refers to the graph to estimate the state in which each observation point is plotted. When only the noise fluorescence is observed, the intercept when the penetration depth is zero becomes equal to or less than a threshold. Therefore, according to the fluorescence reading method, the influence of the noise fluorescence can be considered.

A preferred embodiment of the second aspect of the invention is any of the above-described fluorescence reading method, in which the substrate 2 includes a spot 21 to which the probe substance 1 is fixed, and in which relationships between the penetration depths of the evanescent fields and the fluorescence intensities with respect to a plurality of penetration depths are obtained for a certain spot 21, and then the relationships between the penetration depths of the evanescent fields and the fluorescence intensities with respect to the plurality of penetration depths are obtained for the spot 21 after a predetermined time elapses. According to the fluorescence reading method, a fluorescence intensity of a certain spot can be observed at a plurality of times, so that the temporal change in fluorescence intensity of the spot can be observed. Therefore, the final interaction amount can be predicted while how the interaction such as the hybridization proceeds can be observed.

Embodiment 1

The invention will specifically be described with reference to an embodiment. The invention is not limited to the embodiment, but modifications can appropriately be made based on self-evident matters for those skilled in the art.

Figure 11:
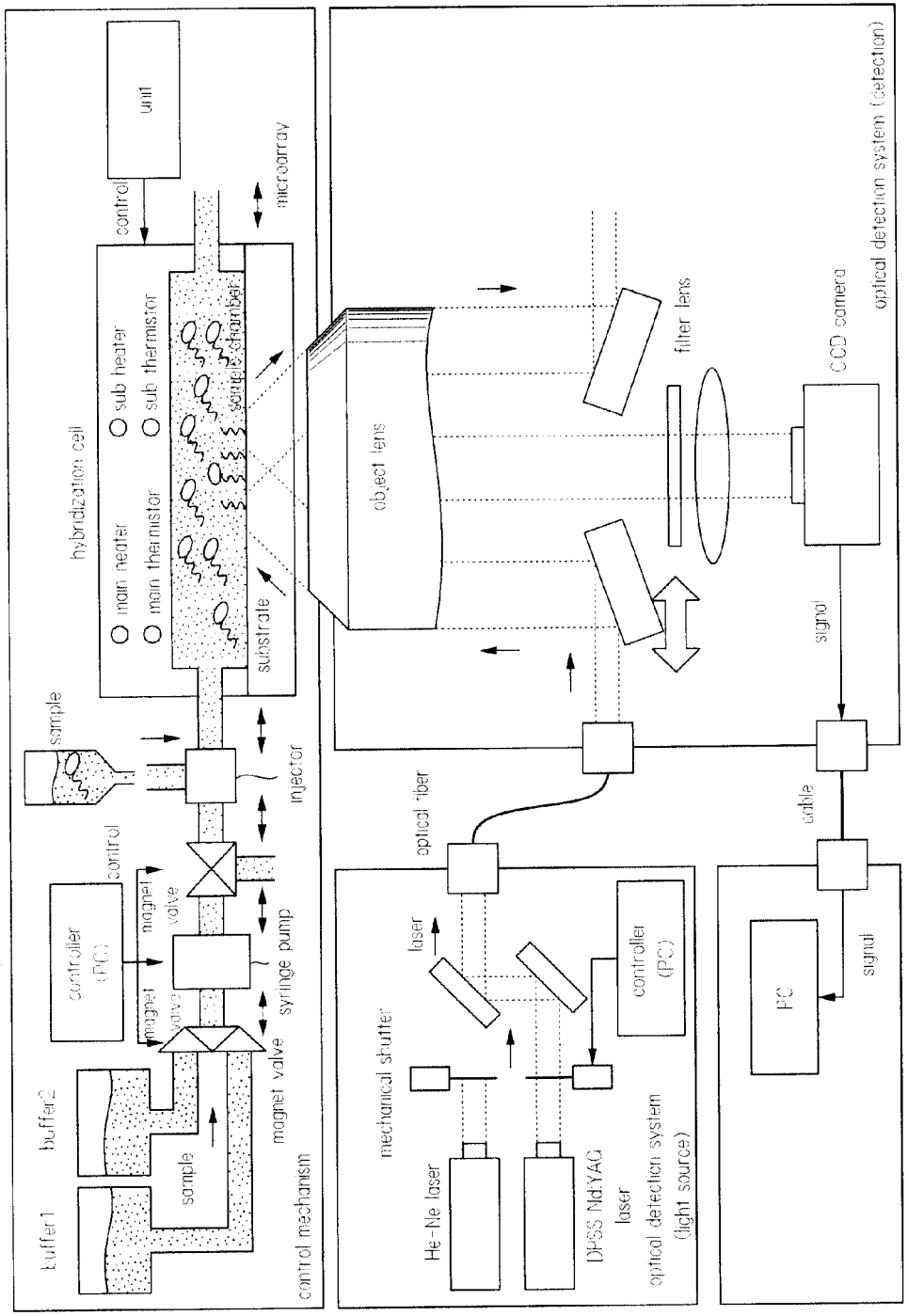
FIG. 11 is a conceptual diagram of an apparatus used in the embodiment.

FIG. 11 is a conceptual diagram for explaining an apparatus used in the embodiment. As illustrated in FIG. 11, a DNA microarray reading apparatus using a flow-through cell is used in this embodiment. The DNA microarray reading apparatus includes a control mechanism that adjusts the sample, a detecting optical system, and a controller such as a personal computer that performs various controls. The detecting optical system includes a light source unit and a detecting unit.

In the control mechanism, the sample containing the target substance is guided to a sample chamber. As illustrated in FIG. 11, the sample is replenished with a buffer as necessary, and the controller controls opening and closing of a solenoid valve and an operation of a syringe pump, which allows the concentration and flow rate of the sample to be controlled. A hybridization cell includes a microarray substrate to which the probe substance is fixed, a sample chamber in which the sample flows, a main thermistor and a sub-thermistor that observe the sample chamber temperature, and a main heater and a sub-heater that control the sample chamber temperature. The sample chamber temperature observed by the thermistor is transmitted to the controller to control the sample chamber temperature. Specifically, when the temperature observed by the thermistor is equal to or lower than a threshold, an instruction to operate the heater is provided, and the heater receiving the instruction generates heat, thereby increasing the sample temperature. When the sample temperature exceeds a predetermined value, the heater stops the heat generation. A plurality of spots are provided in the microarray, and the substrate can be moved in the vertical direction and horizontal direction of FIG. 11 to observe the fluorescence in each spot.

The light source unit of the detecting optical system includes a light source, a mechanical shutter, a mirror, and an optical fiber. A He—Ne laser and a second harmonic of the Nd:YAG laser that is of the DPSS (diode excitation mode) laser are used as the light sources. The mechanical shutter switches ON and OFF of the light emitted from the light sources. The two mirrors are disposed so as to be able to guide the light to the introduction port of the optical fiber whichever one of the light sources is turned on.

The detecting unit of the detecting optical system includes an outgoing end of the optical fiber, a mirror, an objective lens, a filter, and a lens. The light emitted from the light source unit is transmitted to the mirror through the optical fiber. The light reflected by the mirror is incident on the substrate through the objective lens. The incident light is reflected and reflected by the lens through the objective lens. The reflected light may be detected by a detector (not illustrated). Meanwhile, the evanescent field is generated at the boundary between the substrate and the sample chamber by the incident light. The fluorescent substance in the sample chamber is excited by the generated evanescent field to generate the fluorescence. The generated fluorescence reaches the filter through the substrate and the objective lens. The filter weakens the intensity of the light except for the light in the region corresponding to the fluorescence, so that the fluorescence can be extracted. The light passing through the filter is incident on the lens, collected, and incident on the photodetector such as a CCD camera.

The photodetector converts the intensity of the incident light into an electric signal, and transmits the electric signal to the controller such as a computer through a cable. At this point, the image obtained by the observation of the fluorescence may directly be transmitted to the controller. In such case, the controller may analyze the fluorescence intensity based on the input image.

The lens located between the optical fiber and the objective lens can be moved in the example of FIG. 11. The controller can control the moving distance and position of the lens. That is, the controller has a program for grasping the magnitude of the incidence angle to the substrate and the penetration depth of the evanescent field in connection with the lens position, so that the fluorescence intensity in the penetration depth can be recognized. In the example of FIG. 11, in order to realize the autofocus mechanism, the light returned from the objective lens is reflected by the mirror and collected on the CCD element. The objective lens is retained by a piezoelectric actuator having a stroke of 100 μm, and the objective lens is controlled by the computer such that the collective spot position is kept constant on the CCD element.

The fluorescence was actually observed using POPO-3 as the fluorescent substance. In the microarray, the spot had the diameter of 150 μm, and the center distance between each spot was 250 μm.

FIG. 12 shows photographs in place of a drawing illustrating an observed fluorescence image and an microarray when the concentration of a fluorescent substance and an irradiation time are changed, where the concentration is 200 nM and the irradiation time is 817 ms in FIG. 12A, the concentration is 20 nM and the irradiation time is 1.87 s in FIG. 12B, and the concentration is 10 nM and the irradiation time is 4.13 s in FIG. 12C. FIG. 13 shows photographs in place of a drawing illustrating an observed fluorescence image and a microarray when the concentration of a fluorescent substance and an irradiation time are changed, where the concentration is 5 nM and the irradiation time is 4.13 s in FIG. 13A, the concentration is 2 nM and the irradiation time is 9.31 s in FIG. 13B, and the concentration is 1 nM and the irradiation time is 9.31 s in FIG. 13C.

As can be seen from FIGS. 12 and 13, when the fluorescent substance has low concentration, the effective observation may not be performed even in the sufficient irradiation time. Therefore, desirably the concentration of the fluorescent substance is appropriately adjusted depending on the type of the used fluorescent substance or target substance. Typically, the concentration of the fluorescent substance is preferably set to 5 nM or more.

FIGS. 14A and 14B are photographs in place of a drawing illustrating an example of the observed fluorescence image, where a penetration depth is 194 nm in FIG. 14A, and the penetration depth is 94 nm in FIG. 14B. As can be seen from FIG. 14, in the actually-observed fluorescence image, the fluorescence intensity from the outside of the spot is stronger than the fluorescence intensity from the inside of the spot.

FIGS. 15A to 15G are photographs in place of a drawing illustrating an example of the observed fluorescence image when the penetration depth is changed, where the penetration depth is 94 nm in FIG. 15A, the penetration depth is 101 nm in FIG. 15B, the penetration depth is 108 nm in FIG. 15C, the penetration depth is 113 nm in FIG. 15D, the penetration depth is 123 nm in FIG. 15E, the penetration depth is 143 nm in FIG. 15F, and the penetration depth is 194 nm in FIG. 15G.

As can be seen from FIG. 15, a large number of fluorescent molecules adsorbed to the substrate surface are located within 100 nm from the substrate surface. On the other hand, in the region over 100 nm from the substrate surface, the fluorescence derived from the fluorescent molecules adsorbed to the substrate surface cannot be observed. Thus, according to the invention, not only the fluorescence intensity from the molecules bonded to the substrate surface can be detected, but also the fluorescence intensity distribution can be obtained.

Figure 16:
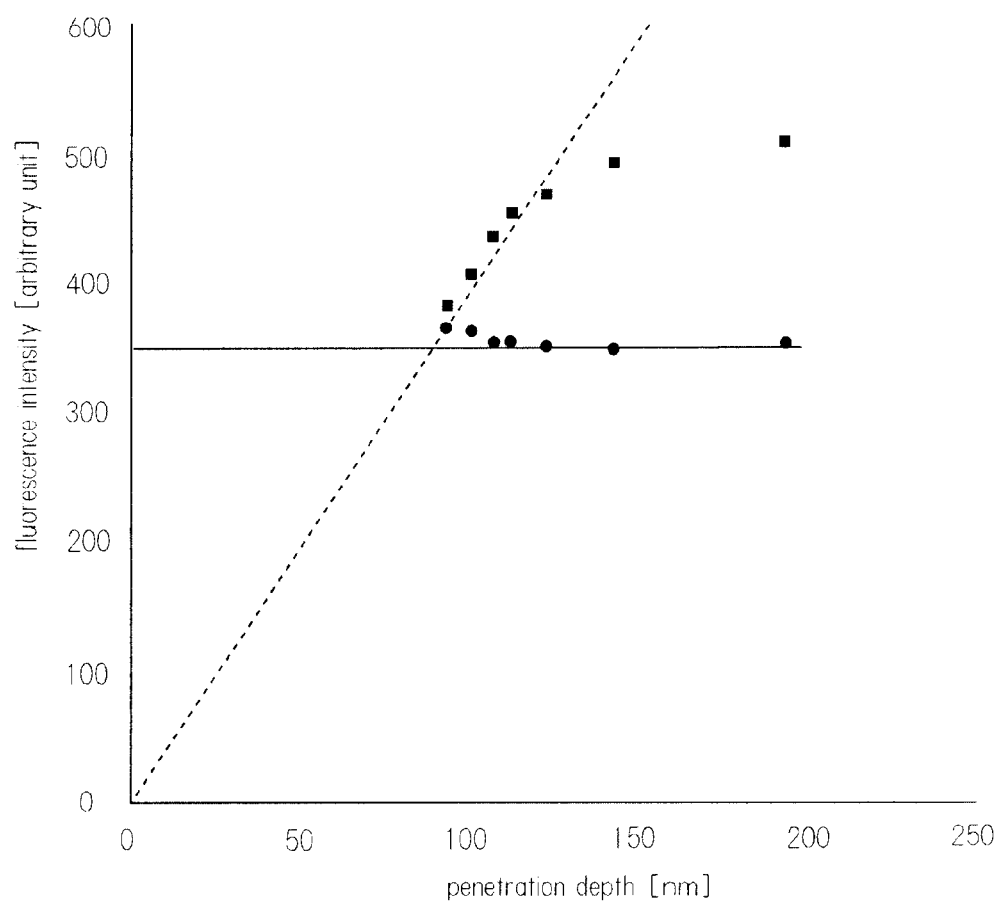
FIG. 16 is a graph illustrating a relationship between the penetration depth and the fluorescence intensity inside and outside a spot in each fluorescence image of FIG. 15.

FIG. 16 is a graph illustrating a relationship between the penetration depth and the fluorescence intensity inside and outside the spot in each fluorescence image of FIG. 15. In FIG. 16, black dots indicate the observation points inside the spot, and squares indicate the observation points outside the spot. A solid line in the graph is an approximate straight line that is obtained by a least square method using the observation points inside the spot in the penetration depths of 94 nm, 108 nm, and 123 nm. On the other hand, a dotted line in FIG. 16 is an approximate straight line that is obtained in a similar manner using the observation points outside the spot.

As can be seen from FIG. 16, the intercept of the plotted straight line substantially becomes zero in the region outside the spot, where the target substance and the probe substance do not interact with each other. On the other hand, in the region inside the spot, where the target substance and the probe substance interact with each other, although the fluorescence intensity is weaker than that of the outside of the spot, the intercept of the straight line in which the observation points are plotted does not become zero but has a large value.

The invention can effectively be applied to various detecting systems in which fluorescence excited by the evanescent field is utilized. Specifically, the invention can effectively be applied to the DNA microarray reading apparatus. Further, the invention can be applied to a protein chip reading apparatus, an apparatus that measures an interaction between proteins, and the like.

The invention claimed is:

1. A fluorescence reading apparatus 12 that detects a specific interaction between a probe substance and a target substance, comprising:

a substrate 2 to which a probe substance 1 is fixed;
a sample chamber 6 that accommodates the probe substance 1 and also accommodates a sample 5 that contains a fluorescent substance 3 and a target substance 4 such that the sample is brought into contact with the probe substance 1;
a light source 7;
an optical system 8 that guides the light from the light source 7 to the substrate 2 to generate an evanescent field; and
a fluorescence detecting unit 9 that detects a fluorescence intensity or a fluorescence image generated by the fluorescent substance 3 excited by the evanescent field,
wherein the optical system 8 comprises an incidence angle adjusting means 10 for adjusting an incidence angle when the light from the light source 7 is incident on the substrate 2;
and a controller 11 that controls an amount of the incidence angle adjusted by the incidence angle adjusting means 10;
wherein the controller 11 comprises a means for receiving information on the incidence angle adjusted by the incidence angle adjusting means 10 and information on the fluorescence intensities or fluorescence images at a plurality of incidence angles detected by the fluorescence detecting unit 9 and obtaining the penetration depths of the evanescent fields with respect to the plurality of incidence angles from the information on the incidence angles; and a means for obtaining information on the fluorescence intensities in the obtained plurality of penetration depths; and
wherein the controller comprises a means for obtaining a graph, using the relationships between the penetration depths of the evanescent fields and the fluorescence intensities with respect to the plurality of penetration depths, where one axis represents the fluorescence intensity while the other axis represents the penetration depth of the evanescent field.

2. The fluorescence reading apparatus 12 as claimed in claim 1,
wherein the optical system 8 comprises an optical element 13 on which the light from the light source 7 is incident; and an objective lens 14 on which the light transmitted through the optical element is incident; and
wherein the incidence angle adjusting means 10 comprises an optical element moving means for moving the optical element 13 such that the position relative to the objective lens 14 is changed.

3. The fluorescence reading apparatus 12 as claimed in claim 1, comprising a substrate moving means 15 for moving the position of the substrate 2.

4. The fluorescence reading apparatus 12 as claimed in claim 1, wherein the controller further comprises:
a means for obtaining a hypothetical fluorescence intensity, using each point on the graph, when the penetration depth of the evanescent field is zero;
a means for comparing a set threshold and the hypothetical fluorescence intensity when the penetration depth of the evanescent field is zero; and
a means for determining whether the probe substance 1 and the target substance 4 have interacted with each other using the comparison result.

5. The fluorescence reading apparatus 12 as claimed in claim 1, wherein the controller comprises a means for observing elapsed time.

6. The fluorescence reading apparatus 12 as claimed in claim 1, wherein not only a connecting pipe, that connects the sample chamber and a sample storage storing the target substance, is connected to the uppermost-stream region of the sample chamber, but also one or more connecting pipes are connected to the midstream region of the sample chamber.

7. The fluorescence reading apparatus 12 as claimed in claim 1, comprising a plurality of objective lenses and also comprising an optical system that guides light to the plurality of objective lenses.

8. The fluorescence reading apparatus 12 as claimed in claim 1, comprising a sample storage storing the target substance and a connecting pipe that connects the sample storage and a plurality of sample chambers, wherein the connecting pipe has a branch portion, and the downstream portions of each connecting pipe branched by the branch portion of the connecting pipe are connected to the plurality of sample chambers respectively.

9. A fluorescence reading apparatus 12 that detects a specific interaction between a probe substance and a target substance, comprising:
a substrate 2 to which a probe substance 1 is fixed;
a sample chamber 6 that accommodates the probe substance 1 and also accommodates a sample 5 that contains a fluorescent substance 3 and a target substance 4 such that the sample is brought into contact with the probe substance 1;
a light source 7;
an optical system 8 that guides the light from the light source 7 to the substrate 2 to generate an evanescent field; and
a fluorescence detecting unit 9 that detects a fluorescence intensity or a fluorescence image generated by the fluorescent substance 3 excited by the evanescent field,
wherein the optical system 8 comprises an incidence angle adjusting means 10 for adjusting an incidence angle when the light from the light source 7 is incident on the substrate 2;
and a controller 11 that controls an amount of the incidence angle adjusted by the incidence angle adjusting means 10,
wherein the controller 11 comprises a means for receiving information on the incidence angle adjusted by the incidence angle adjusting means 10 and information on the fluorescence intensities or fluorescence images at a plurality of incidence angles detected by the fluorescence detecting unit 9 and obtaining the penetration depths of the evanescent fields with respect to the plurality of incidence an angles from the information on the incidence angles; and a means for obtaining information on the fluorescence intensities in the obtained plurality of penetration depths; and
wherein the substrate 2 comprises a spot 21 to which the probe substance 1 is fixed;
wherein the fluorescence detecting unit 9 obtains the fluorescence image generated by the fluorescent substance 3; and
wherein the controller 11 comprises a means for scanning the fluorescence image to compute a boundary 21 at which the fluorescence intensity is changed; a means for grasping a region 23 inside the spot and a region 24 outside the spot in the fluorescence image from the shape of the boundary; and a means for obtaining the fluorescence intensity inside the spot.

10. A fluorescence reading apparatus 12 that detects a specific interaction between a probe substance and a target substance, comprising:
a substrate 2 to which a probe substance 1 is fixed;
a sample chamber 6 that accommodates the probe substance 1 and also accommodates a sample 5 that contains a fluorescent substance 3 and a target substance 4 such that the sample is brought into contact with the probe substance 1;

a light source 7;

an optical system 8 that guides the light from the light source 7 to the substrate 2 to generate an evanescent field; and a fluorescence detecting unit 9 that detects a fluorescence intensity or a fluorescence image generated by the fluorescent substance 3 excited by the evanescent field, wherein the optical system 8 comprises an incidence angle adjusting means 10 for adjusting an incidence angle when the light from the light source 7 is incident on the substrate 2; and a controller 11 that controls an amount of the incidence angle adjusted by the incidence angle adjusting means 10; and wherein the controller 11 comprises a means for receiving information on the incidence angle adjusted by the incidence angle adjusting means 10 and information on the fluorescence intensities or fluorescence images at a plurality of incidence angles detected by the fluorescence detecting unit 9 and obtaining the penetration depths of the evanescent fields with respect to the plurality of incidence angles from the information on the incidence angles; and a means for obtaining information on the fluorescence intensities in the obtained plurality of penetration depths; and wherein the concentration of the probe substance 1 is increased toward the downstream region of the sample chamber in the substrate 2 to which the probe substance is fixed.

11. A fluorescence reading method using a fluorescence reading apparatus that detects a specific interaction between a probe substance and a target substance, comprising:

a substrate 2 to which a probe substance 1 is fixed;

a sample chamber 6 that accommodates the probe substance 1 and also accommodates a sample 5 that contains a fluorescent substance 3 and a target substance 4 such that the sample is brought into contact with the probe substance 1;

a light source 7;

an optical system 8 that guides the light from the light source 7 to the substrate 2 to generate an evanescent field; and a fluorescence detecting unit 9 that detects a fluorescence intensity or a fluorescence image generated by the fluorescent substance 3 excited by the evanescent field, characterized in that a step of changing the penetration depth of the evanescent field and a step of obtaining the fluorescence intensity after the penetration depth of the evanescent field is changed are repeatedly performed to obtain the fluorescence intensities in a plurality of penetration depths of the evanescent fields, wherein a graph is obtained where one axis represents the fluorescence intensity while the other axis represents the penetration depth of the evanescent field, using the relationships between the penetration depths of the evanescent fields and the fluorescence intensities with respect to the plurality of penetration depths.

12. A fluorescence reading method as claimed in claim 9, wherein, in the step of changing the penetration depth of the evanescent field, the penetration depth of the evanescent field is changed by adjusting the incidence angle of the light incident on the substrate 2.

13. A fluorescence reading method as claimed in claim 9, wherein the substrate (2) comprises a spot 21 to which the probe substance 1 is fixed; and wherein the relationships between the penetration depths of the evanescent fields and the fluorescence intensities with respect to the plurality of penetration depths are obtained for a certain spot 21 and then the relationships between the penetration depths of the evanescent fields and the fluorescence intensities with respect to the plurality of penetration depths are obtained for the spot 21 after a predetermined time has elapsed.

14. A fluorescence reading apparatus 12 that detects a specific interaction between a probe substance and a target substance, comprising:

a substrate 2 to which a probe substance 1 is fixed;

a sample chamber 6 that accommodates the probe substance 1 and also accommodates a sample 5 that contains a fluorescent substance 3 and a target substance 4 such that the sample is brought into contact with the probe substance 1;

a light source 7;

an optical system 8 that guides the light from the light source 7 to the substrate 2 to generate an evanescent field; and a fluorescence detecting unit 9 that detects a fluorescence intensity or a fluorescence image generated by the fluorescent substance 3 excited by the evanescent field, characterized in that the concentration of the probe substance 1 is increased toward the downstream region of the sample chamber in the substrate 2 to which the probe substance is fixed.

* * * * *